US009329109B2

(12) United States Patent
Fukuda et al.

(10) Patent No.: US 9,329,109 B2
(45) Date of Patent: *May 3, 2016

(54) CELL PROCESSING APPARATUS, SAMPLE PREPARATION APPARATUS, AND CELL ANALYZER

(71) Applicant: Sysmex Corporation, Kobe-shi, Hyogo (JP)

(72) Inventors: Masakazu Fukuda, Kobe (JP); Hironori Kobayashi, Ono (JP); Junyi Ding, Kobe (JP); Ryuichiro Ebi, Osaka (JP); Koki Tajima, Kobe (JP)

(73) Assignee: Sysmex Corporation (JP)

( * ) Notice: Subject to any disclaimer, the term of this patent is extended or adjusted under 35 U.S.C. 154(b) by 248 days.

This patent is subject to a terminal disclaimer.

(21) Appl. No.: 13/787,211

(22) Filed: Mar. 6, 2013

(65) Prior Publication Data

US 2013/0183747 A1 Jul. 18, 2013

Related U.S. Application Data

(63) Continuation of application No. 12/892,579, filed on Sep. 28, 2010, now Pat. No. 8,415,145, which is a continuation of application No. PCT/JP2009/056071, filed on Mar. 26, 2009.

(30) Foreign Application Priority Data

Mar. 31, 2008 (JP) ................................ 2008-089863
Mar. 31, 2008 (JP) ................................ 2008-089868

(51) Int. Cl.
*C12M 1/34* (2006.01)
*G01N 1/34* (2006.01)
(Continued)

(52) U.S. Cl.
CPC ................ *G01N 1/34* (2013.01); *G01N 15/147* (2013.01); *G01N 15/1475* (2013.01); *G01N 35/1095* (2013.01); *G01N 15/0618* (2013.01);
(Continued)

(58) Field of Classification Search
CPC ................ G01N 15/0618; G01N 2035/00475
See application file for complete search history.

(56) References Cited

U.S. PATENT DOCUMENTS 5,269,918 A 12/1993 Lapidus et al.
5,560,889 A 10/1996 Ogino
(Continued)

FOREIGN PATENT DOCUMENTS

JP 06-221976 A 8/1994
JP 07-051521 A 2/1995
(Continued)

OTHER PUBLICATIONS

International Search Report for International Application No. PCT/JP2009/056071, dated Jun. 23, 2009, 4 pages.

*Primary Examiner* — William H Beisner
(74) *Attorney, Agent, or Firm* — Brinks Gilson & Lione

(57) ABSTRACT

A cell processing apparatus includes a storage container that contains liquid L including a biological sample; a filter that prevents a first cell C1 in the biological sample from passing and allows a second cell C2 having a smaller diameter than that of the first cell C1 to pass; and a filtration cylinder for separating, in the storage container and via the filter, the liquid L into a first liquid L1 mainly including the first cell C1 and a second liquid L2 mainly including the second cell C2. A measurement target cell filtered by the filter among other cells can be easily collected.

19 Claims, 15 Drawing Sheets

(51) Int. Cl.
  G01N 15/14 (2006.01)
  G01N 35/10 (2006.01)
  G01N 15/06 (2006.01)
  G01N 35/00 (2006.01)
  G01N 15/10 (2006.01)

(52) U.S. Cl.
  CPC  *G01N2015/1006* (2013.01); *G01N 2015/1493* (2013.01); *G01N 2035/00475* (2013.01)

(56) References Cited

U.S. PATENT DOCUMENTS

| | | | |
|---|---|---|---|
| 6,312,950 | B1 | 11/2001 | Ohmura et al. |
| 6,372,447 | B1 | 4/2002 | Raz |
| 8,415,145 | B2 * | 4/2013 | Fukuda et al. ............. 435/308.1 |
| 2004/0069714 | A1 | 4/2004 | Ferguson |
| 2007/0278154 | A1 | 12/2007 | Naqaoka et al. |
| 2008/0108103 | A1 | 5/2008 | Ishisaka et al. |
| 2008/0158543 | A1 | 7/2008 | Puskas et al. |
| 2011/0014685 | A1 | 1/2011 | Fukuda et al. |

FOREIGN PATENT DOCUMENTS

| | | |
|---|---|---|
| JP | 2000-146782 A | 5/2000 |
| JP | 2005-102648 A | 4/2005 |
| JP | 2007-319019 A | 12/2007 |
| WO | WO 2006/103920 A1 | 10/2006 |
| WO | WO 2009122999 A1 * | 10/2009 ........... G01N 15/147 |

* cited by examiner

CELL PROCESSING APPARATUS, SAMPLE PREPARATION APPARATUS, AND CELL ANALYZER

RELATED APPLICATIONS

This application is a continuation of U.S. patent application Ser. No. 12/892,579 filed on Sep. 28, 2010 and issued on Apr. 9, 2013 as U.S. Pat. No. 8,415,145, which is a continuation of PCT/JP2009/056071 filed on Mar. 26, 2009, which claims priority to Japanese Application Nos. JP2008-089863 and JP2008-089868 both filed on Mar. 31, 2008. The entire contents of these applications are incorporated herein by reference.

BACKGROUND OF THE INVENTION

1. Technical Field

The present invention relates to a cell processing apparatus, a sample preparation apparatus, and a cell analyzer.

Specifically, the present invention relates to a technique for easily collecting a measurement target cell that is discriminated by a filter from other cells.

2. Background Art

Conventionally, as a cell analyzer for analyzing cells included in a biological sample extracted from a living body, there has been known a cell analyzer in which epidermal cells of a cervix included in a sample extracted from the cervix of a subject are measured by a flow cytometer to perform the screening of cancer cells and atypical cells (e.g., see the pamphlet of International Publication No. 2006/103920).

In the case of the cell analyzer disclosed in the above pamphlet, an epidermal cell of a cervix is assumed as a measurement target. A sample extracted from a cervix includes not only an epidermal cell but also cells such as red blood cells and white blood cells. If the sample is measured without any processing, the measurement result is influenced by the cells such as red blood cells or the white blood cells. This may prevent an accurate screening of cancer and atypical cells.

Thus, there has been required a technique for discriminating a measurement target cell and cells other than the measurement target cell to easily collect only the measurement target cell.

As a technique for performing the above collection, a cell separation/collection apparatus has been known for example in which cell suspension liquid including blood cells is allowed to flow on a filter and a lymphocyte as a measurement target cell is captured by the filter. Then, liquid including other cells such as red blood cells or white blood cells is discharged through the filter and collection liquid is then supplied to the filter to collect lymphocytes captured by the filter (for example, see U.S. Pat. No. 6,312,950).

However, in the case of the above cell separation/collection apparatus disclosed in U.S. Pat. No. 6,312,950, only a lymphocyte is captured by an upper face of the filter. However, liquid that included the lymphocyte is discharged to the outside through the filter, thus requiring an operation to additionally separate the lymphocyte attached to the filter to collect the lymphocyte.

Thus, in the case of the cell separation/collection apparatus disclosed in U.S. Pat. No. 6,312,950, a disadvantage is caused where the separation of a lymphocyte from a filter requires an operation to change a cavity rate of the filter to a cavity rate different from that used to capture a lymphocyte and an operation to supply collection liquid to the filter, thus requiring a complicated mechanism.

It is noted that, a technique also has been known by which, when a measurement target cell has a smaller diameter than those of other cells, sample liquid including a measurement target cell is sent to a filter, and the liquid including the measurement target cell is allowed to pass through the filter and is collected, and other cells are captured by the filter and are discharged.

However, this technique allows the measurement target cell to pass through the filter. Thus, this technique cannot be used to a case as in an epidermal cell where a measurement target cell has a larger diameter than those of other cells.

SUMMARY OF THE INVENTION

The scope of the present invention is defined solely by the appended claims, and is not affected to any degree by the statements within this summary.

A first aspect of the present invention is a sample preparation apparatus comprising: a storage container that can contain liquid including a biological sample; a filter that prevents a first cell in the biological sample from passing therethrough and that allows a second cell having a smaller diameter than that of the first cell to pass therethrough; a liquid separation section for separating, in the storage container and via the filter, the liquid into a first liquid mainly including the first cell and a second liquid mainly including the second cell, so that the first liquid is below the filter while the second liquid is above the filter; a liquid acquisition section for acquiring the first liquid separated so as to be below the filter by the liquid separation section; and a sample preparation section for preparing a measurement sample from the first liquid acquired by the liquid acquisition section and a predetermined reagent.

A second aspect of the present invention is a cell analyzer comprising: a storage container that can contain liquid including a biological sample; a filter that prevents a first cell in the biological sample from passing therethrough and that allows a second cell having a smaller diameter than that of the first cell to pass therethrough; a liquid separation section for separating, in the storage container and via the filter, the liquid into a first liquid mainly including the first cell and a second liquid mainly including the second cell, so that the first liquid is below the filter while the second liquid is above the filter; a liquid acquisition section for acquiring the first liquid separated so as to be below the filter by the liquid separation section; a detection section for detecting the first cell from the first liquid acquired by the liquid acquisition section; and an analysis section for analyzing the first cell based on a detection result by the detection section.

A third aspect of the present invention is a cell processing apparatus comprising: a storage container that can contain liquid including a biological sample; a filter that prevents a first cell in the biological sample from passing therethrough and that allows a second cell having a smaller diameter than that of the first cell to pass therethrough; a liquid separation section for separating, in the storage container and via the filter, the liquid into a first liquid mainly including the first cell and a second liquid mainly including the second cell, so that the first liquid is below the filter while the second liquid is above the filter; and a liquid acquisition section for acquiring the first liquid separated so as to be below the filter by the liquid separation section.

DETAILED DESCRIPTION OF THE PREFERRED EMBODIMENTS

The following section will describe an embodiment of the cell analyzer and the cell analysis method of the present invention with reference to the attached drawings.

[First Embodiment]
[Entire Configuration of Cell Analyzer]

Figure 1:
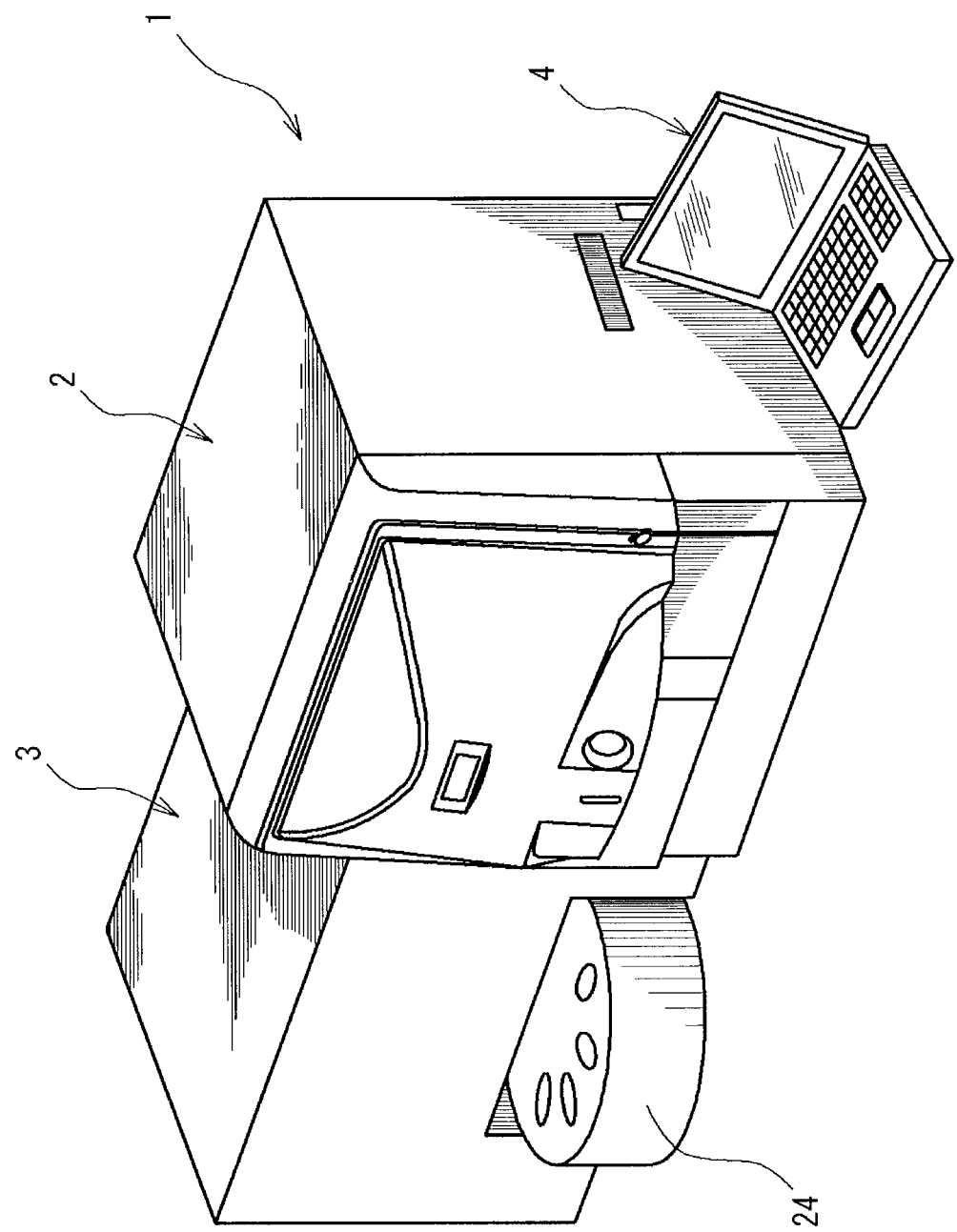
FIG. 1 is a perspective view illustrating a cell analyzer according to the first embodiment.

FIG. 1 is a perspective view illustrating a cell analyzer 1 according to the first embodiment of the present invention.

This cell analyzer 1 causes a measurement sample including cells extracted from a patient to flow in a flow cell, emits laser beam to the measurement sample flowing in the flow cell, detects the light from the measurement sample (e.g., forward scattered light, side fluorescence) to analyze the optical signal to thereby determine whether the cells include a cancer cell or not.

More specifically, the cell analyzer 1 of the present embodiment is used to analyze epidermal cells of a cervix and is used to screen a cervical cancer.

As shown in FIG. 1, the cell analyzer 1 comprises: a measurement apparatus 2 for subjecting a measurement sample to an optical measurement by laser beam; a sample preparation apparatus 3 for subjecting a biological sample extracted from a subject to a preprocessing (e.g., cleaning or staining) to prepare a measurement sample to be supplied to the measurement apparatus 2; and a data processing apparatus 4 for analyzing the measurement result by the measurement apparatus 2 for example.

[Internal Configuration of Measurement Apparatus]

Figure 2:
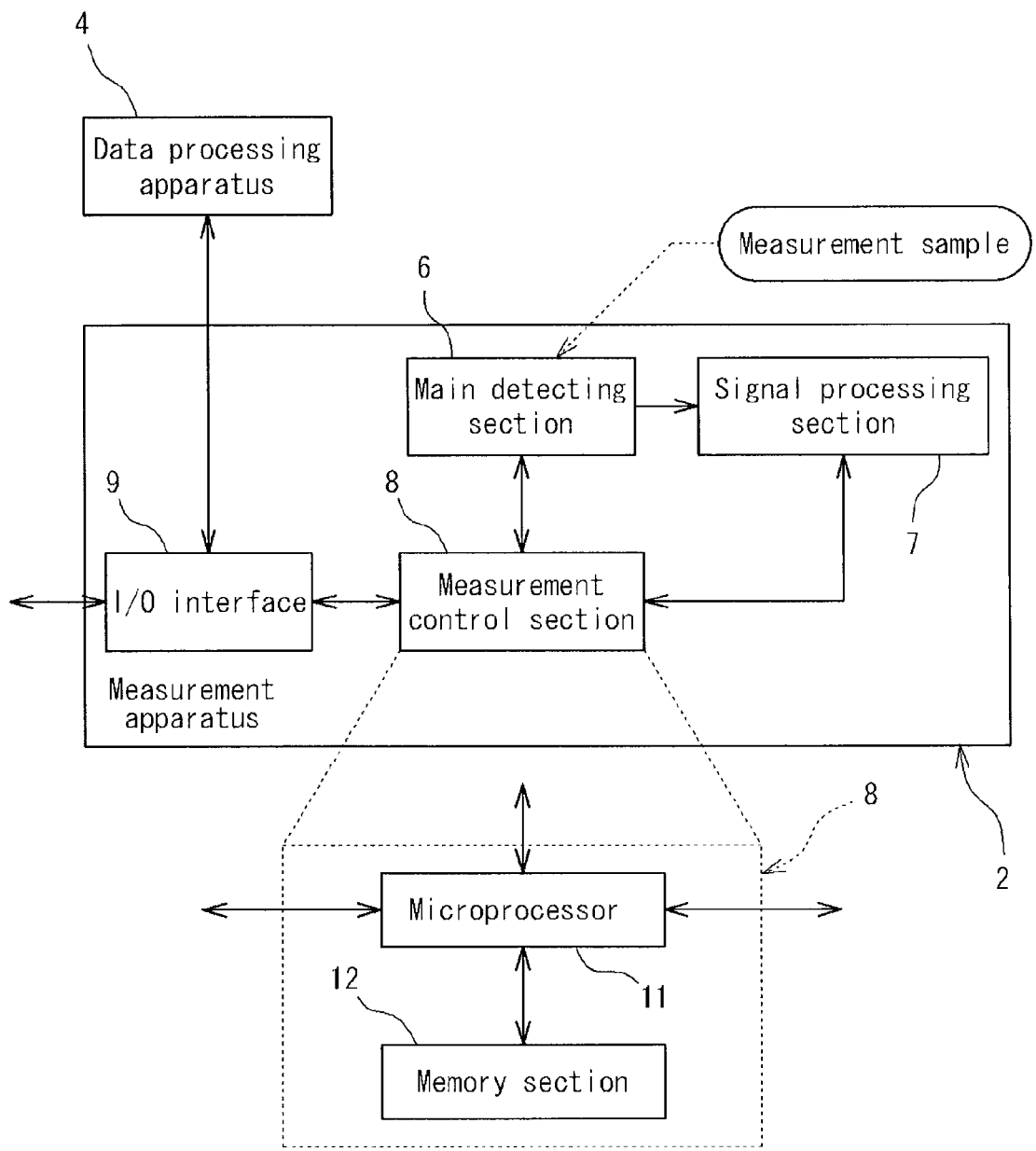
FIG. 2 is a block diagram illustrating the internal configuration of a measurement apparatus.

FIG. 2 is a block diagram illustrating the internal configuration of the measurement apparatus 2.

As shown in FIG. 2, this measurement apparatus 2 comprises: a main detecting section 6; a signal processing section 7; a measurement control section 8; and an I/O interface 9.

Figure 5:
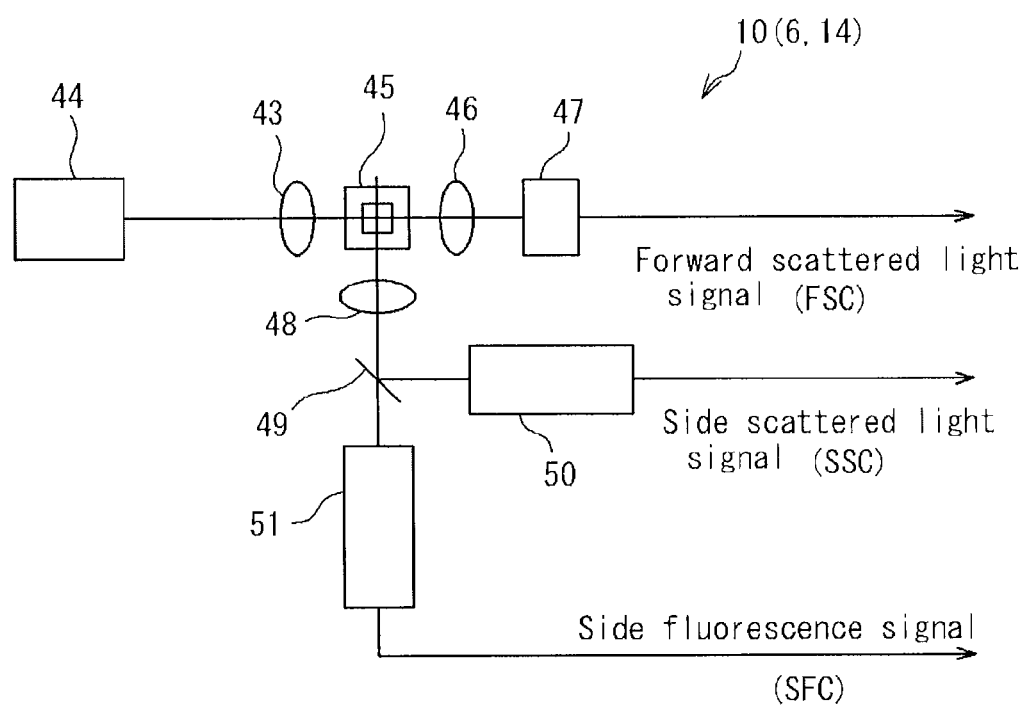
FIG. 5 is a function block diagram of a flow cytometer configuring a main detecting section.
Figure 6:
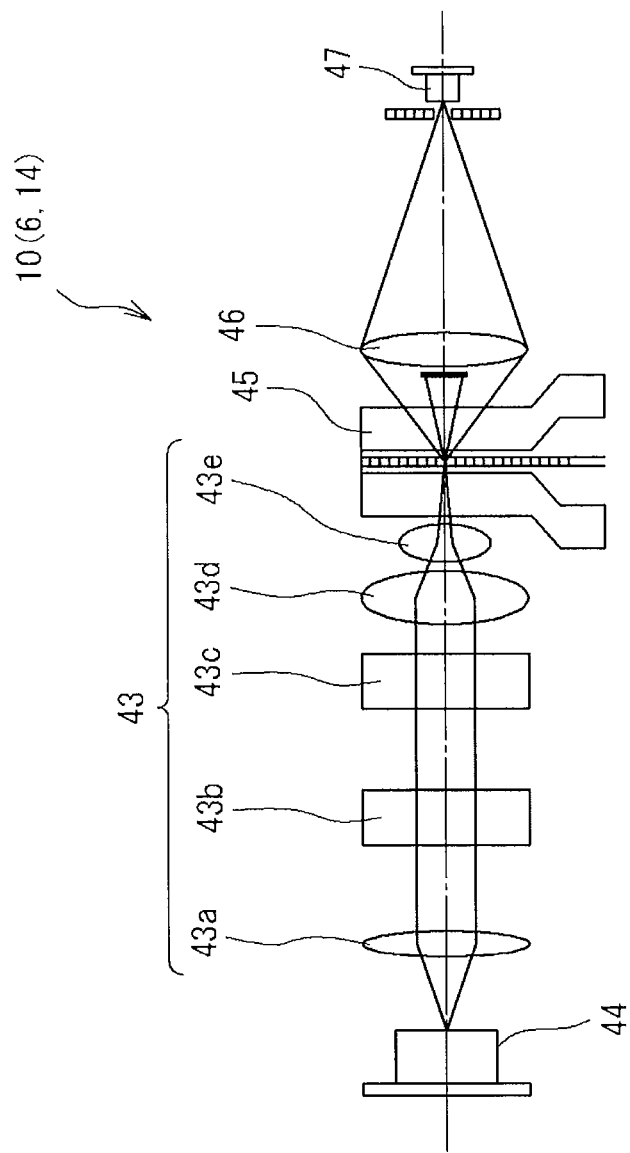
FIG. 6 is a side view illustrating an optical system of the flow cytometer.

Among these components, the main detecting section 6 detects, from a measurement sample, the number and size of a measurement target cell as well as the nucleus thereof for example. In the present embodiment, a flow cytometer 10 shown in FIG. 5 and FIG. 6 is used.

The signal processing section 7 is composed of a signal processing circuit that performs a signal processing required for an output signal from the main detection section 6. The measurement control section 8 includes a microprocessor 11 and a memory section 12. The memory section 12 is composed of ROM and RAM for example.

The memory section 12 includes a ROM that stores therein control programs for controlling the operations of the main detecting section 6 and the signal processing section 7 and data required to execute the control programs. The microprocessor 11 can load the control programs to a RAM or can execute the programs directly from the ROM.

The microprocessor 11 of the measurement control section 8 is connected, via the I/O interface 9, to the data processing apparatus 4 and a microprocessor 19 of a preparation control section 16 which will be described later. Thus, the data processed by the microprocessor 11 and the data required for the processing by the microprocessor 11 can be sent and received between the data processing apparatus 4 and the microprocessor 19 of the preparation control section 16.

[Internal Configuration of Sample Preparation Apparatus]

Figure 3:
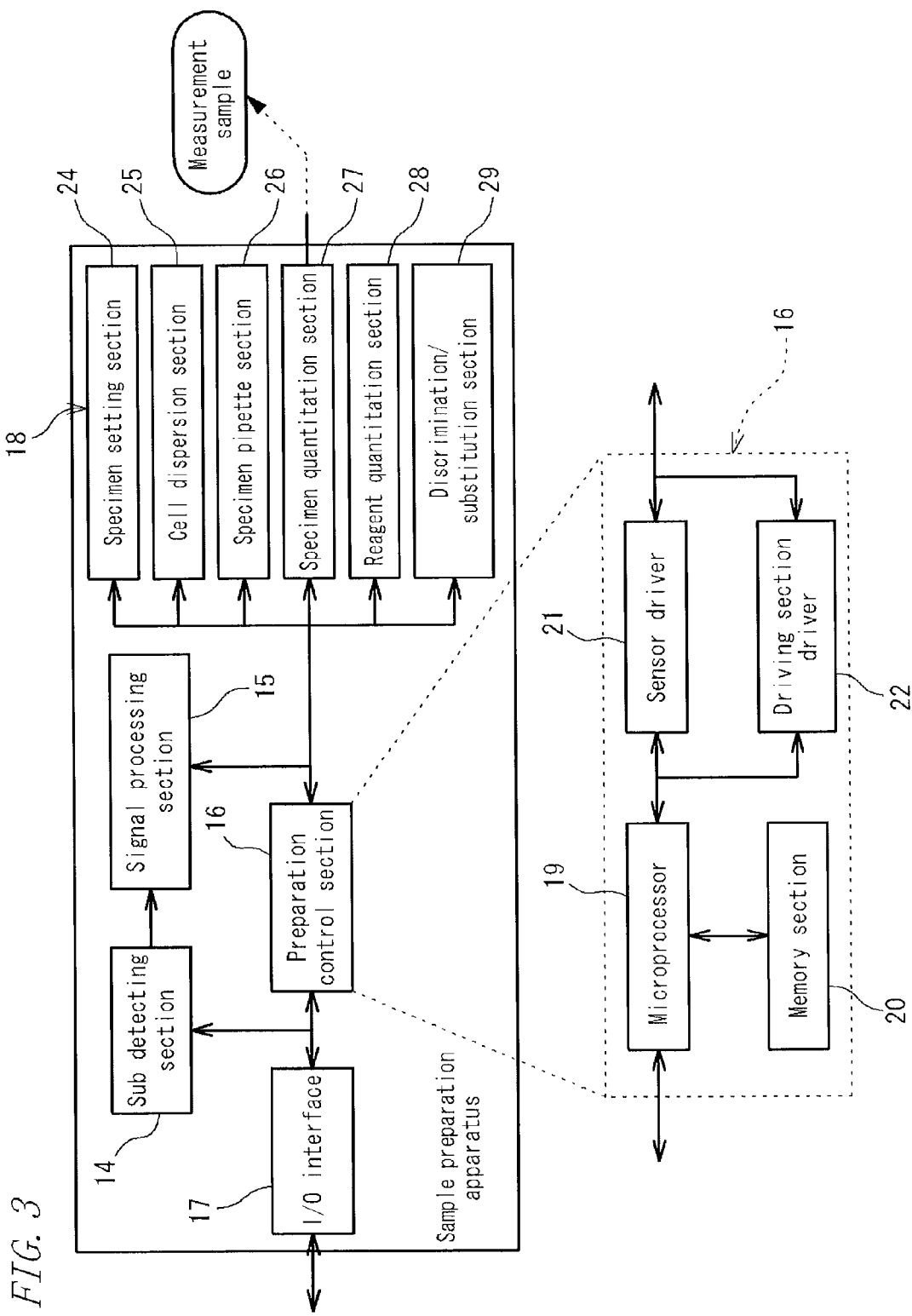
FIG. 3 is a block diagram illustrating the internal configuration of a sample preparation apparatus.

FIG. 3 is a block diagram illustrating the internal configuration of the sample preparation apparatus 3.

As shown in FIG. 3, this sample preparation apparatus 3 comprises: a sub detecting section 14; a signal processing section 15; the preparation control section 16; an I/O interface 17; and a preparation device section 18 for automatically subjecting a biological sample to a component adjustment.

Among them, the sub detecting section 14 detects the number of measurement target cells included in the biological sample. In the present embodiment, the sub detecting section 14 also uses substantially the same flow cytometer 10 as those shown in FIG. 5 and FIG. 6.

The signal processing section 15 is composed of a signal processing circuit to perform a signal processing required for an output signal from the sub detecting section 14. The preparation control section 16 is composed of: the microprocessor 19; a memory section 20; a sensor driver 21; and a driving section driver 22. The memory section 20 is composed of ROM and RAM for example.

The preparation device section 18 of the present embodiment is composed of: a specimen setting section 24; a cell dispersion section 25; a specimen pipette section 26; a specimen quantitation section 27; a reagent quantitation section 28; and a discrimination/substitution section 29.

Among them, the specimen setting section 24 is used to set a plurality of living body containers 53 and product containers 54 (see FIG. 7) that store biological samples extracted from a patient and preservative solution containing methanol as a major component. The cell dispersion section 25 agitates mixed liquid of the biological sample and the preservative solution in the living body container 53 to forcedly disperse the cells included in the sample.

The specimen pipette section 26 is used to remove the mixed liquid of the biological sample and the preservative solution in which the cells are dispersed from the living body container 53 to introduce the liquid to the fluid circuit of the preparation device section 18 or is used to return a prepared product to the product container 54 or to remove the product from the product container 54. The specimen quantitation section 27 quantifies the mixed liquid of the biological sample and the preservative solution supplied to the fluid circuit.

The reagent quantitation section 28 quantifies the reagent added to a biological sample such as staining fluid. The discrimination/substitution section 29 is used to mix the biological sample with the preservative solution and the diluted solution to substitute the preservative solution and the diluted solution, and to discriminate the measurement target cell from cells other than the measurement target cell (e.g., red blood cells, white blood cells) and bacteria for example. It is noted that the configuration of the fluid circuit of the preparation device section 18 having the above respective sections 24 to 29 (FIG. 7) will be described later.

The ROM of the memory section 20 stores therein the control programs used to control the operations of the sub detecting section 14, the signal processing section 15, the sensor driver 21, and the driving section driver 22 and the data required to execute the control programs. The control program can be loaded by the microprocessor 19 to the RAM for execution or can be directly executed from the ROM.

The microprocessor 19 of the preparation control section 16 is connected, via the I/O interface 17, to the microprocessor 11 of the measurement control section 8. Thus, the data processed by the microprocessor 19 and the data required for the processing by the microprocessor 19 can be sent and received between the microprocessor 19 and the microprocessor 11 of the measurement processing section 8.

The microprocessor 19 of the preparation control section 16 is connected, via the sensor driver 21 and the driving section driver 22, to the sensors or the like of the respective sections 24 to 29 of the preparation device section 18 and a driving motor configuring a driving section. Based on a sensing signal from a sensor, the microprocessor 19 executes a control program to control the operation of the driving section.

[Internal Configuration of Data Processing Section]

Figure 4:
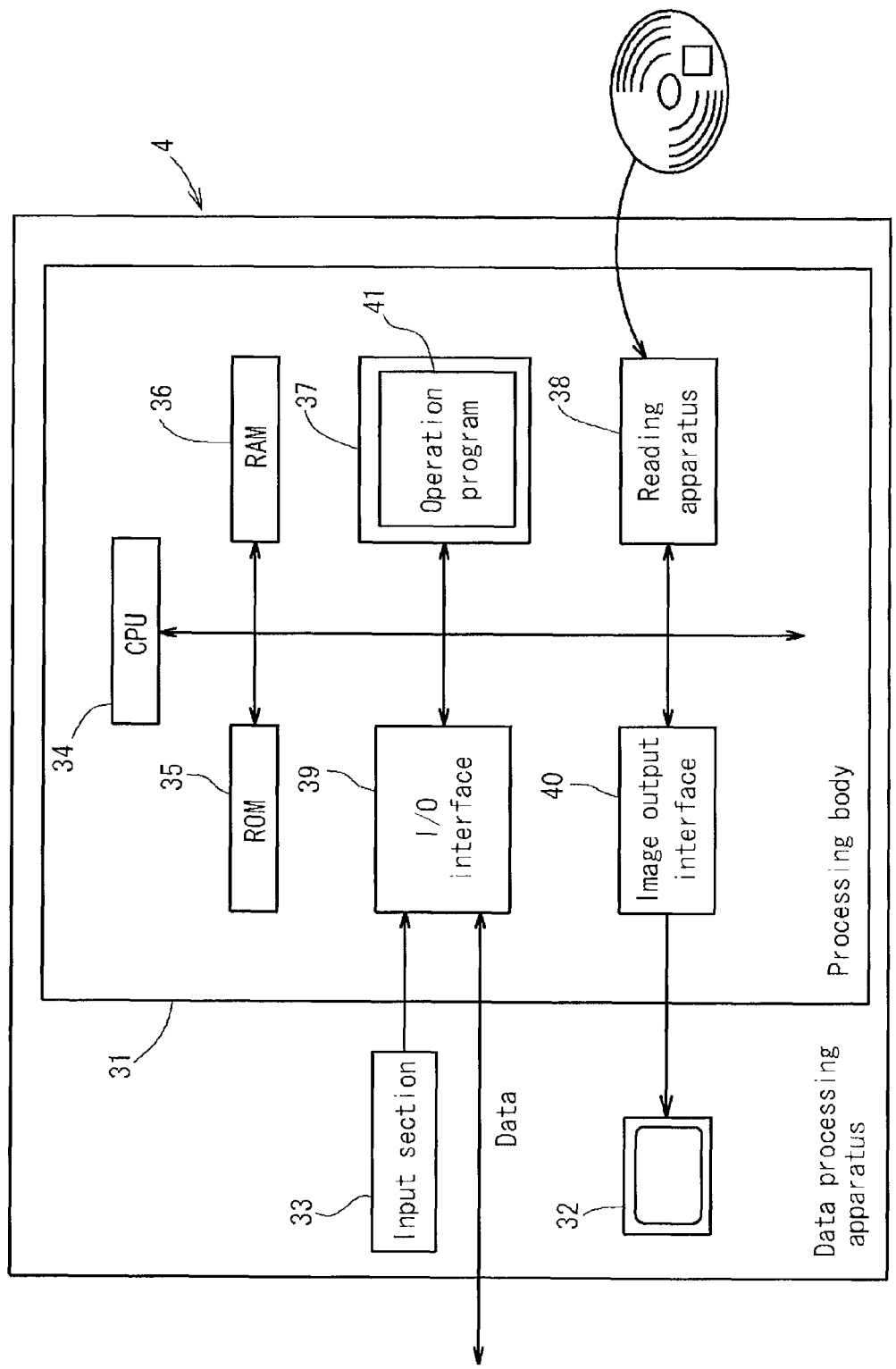
FIG. 4 is a block diagram illustrating the internal configuration of a data processing apparatus.

FIG. 4 is a block diagram illustrating the internal configuration of the data processing apparatus 4.

As shown in FIG. 4, the data processing apparatus 4 of the present embodiment is composed of, for example a personal computer such as a laptop PC (or a desk top PC) and is mainly composed of a processing body 31, a display section 32, and an input section 33.

The processing body 31 comprises: a CPU 34; a ROM 35; a RAM 36; a hard disk 37; a reading apparatus 38; an input/output interface 39; and an image output interface 40. The respective sections are connected via an internal bus so that these sections can communicate to one another.

The CPU 34 can execute a computer program memorized in the ROM 35 and a computer program loaded to the RAM 36.

The ROM 35 is configured by a mask ROM, PROM, EPROM, EEPROM or the like and stores therein a computer program executed by the CPU 34 and the data used for the computer program for example.

The RAM 36 is configured by SRAM or DRAM for example. The RAM 36 is used to read various computer programs recorded in the ROM 35 and the hard disk 37 and is used as a working region of the CPU 34 to execute these computer programs.

In the hard disk 37, various computer programs to be executed by the CPU 34 such as an operating system and an application program and the data used to execute the programs are installed In the hard disk 37, there is installed an operating system that provides, for example, a graphical user interface environment such as Windows® manufactured and sold by U.S. Microsoft Corporation.

Furthermore, in the hard disk 37, an operation program 41 is installed for the transmission of an operation instruction to the measurement control section 8 and the preparation control section 16, for the reception and analysis processings of the measurement result performed by the measurement apparatus 2, and for the display of the processed analysis result. The operation program 41 operates on the operating system.

The reading apparatus 38 is configured by a flexible disk drive, a CD-ROM drive, or a DVD-ROM drive and can read a computer program or data recorded in a portable recording medium.

The input/output interface 39 is composed of, for example, a serial interface such as USB, IEEE1394 or RS-232C, a parallel interface such as SCSI, IDE or IEEE1284, and an analog interface such as a D/A converter or an A/D converter.

The input/output interface 39 is connected to the input section 33 composed of a keyboard and a mouse. By allowing a user to operate the input section 33, data can be inputted to the computer.

The input/output interface 39 is also connected to the I/O interface 9 of the measurement apparatus 2 to thereby provide data transmission and reception between the measurement apparatus 2 and the data processing apparatus 4.

The image output interface 40 is connected to the display section 32 composed of LCD or CRT. The image output interface 40 causes the display section 32 to output a video signal depending on the image data from the CPU 34.

[Configuration of Main Detecting Section (Flow Cytometer)]

FIG. 5 is a function block diagram of the flow cytometer 10 configuring the main detecting section 6. FIG. 6 is a side view illustrating the optical system of the flow cytometer 10.

As shown in FIG. 5, the flow cytometer 10 has a lens system 43 that collects the laser beam from a semiconductor laser 44 as a light source to a measurement sample flowing in a flow cell 45. A collecting lens 46 collects the forward scattered light from cells in the measurement sample to a scattered light detector composed of a photodiode 47.

Although FIG. 5 shows the lens system 43 by a single lens, the lens system 43 actually has a configuration as shown in FIG. 6 for example.

In other words, the lens system 43 of the present embodiment is composed of, in an order from the semiconductor laser 44 (left side of FIG. 6), a collimator lens 43a, a cylinder lens system (a planoconvex cylinder lens 43b+a biconcave cylinder lens 43c) and a condenser lens system (a condenser lens 43d+a condenser lens 43e).

Returning to FIG. 5, a side collecting lens 48 collects the side scattered light and the side fluorescence in the measurement target cell or the nucleus in the cell to a dichroic mirror 49. The mirror 49 reflects the side scattered light to the photomultiplier 50 as a scattered light detector and transmits the side fluorescence to a photomultiplier 51 as a fluorescence detector. These lights reflect the features of the cell in the measurement sample or the nucleus.

Then, the photodiode 47 as well as the respective photomultipliers 50 and 51 convert the received optical signal to an electric signal to output a forward scattered light signal (FSC), a side scattered light signal (SSC), and a side fluorescence signal (SFL), respectively. These output signals are amplified by a preamplifier (not shown) and is sent to the signal processing section 7 of the measurement apparatus 2 (FIG. 2).

The respective signals FSC, SSC, and SFL processed by the signal processing section 7 of the measurement apparatus 2 are sent by the microprocessor 11 from the I/O interface 9 to the data processing apparatus 4.

The CPU 34 of the data processing apparatus 4 executes the operation program 41 to thereby prepare a scattergram for analyzing the cell and nucleus based on the respective signals FSC, SSC, and SFL. Based on the scattergram, it is determined whether the cell in the measurement sample is abnormal or not, specifically, whether the cell is a cancerous cell or not.

It is noted that, although the flow cytometer 10 may have a light source composed of a gas laser instead of the semiconductor laser 44, the use of the semiconductor laser 44 is preferred from the viewpoints of low cost, small size, and low power consumption. The use of the semiconductor laser 44 as described above can reduce the product cost and can allow the apparatus to have a small size and power saving.

Furthermore, in the present embodiment, blue semiconductor laser having a short wavelength is used that is advantageously used to narrow beam. The blue semiconductor laser is also advantageous to a fluorescence excitation wavelength such as PI. It is noted that red semiconductor laser also may be used that is low-cost and long-life among semiconductor lasers and that can be supplied stably from manufacturers.

By the way, an epidermal cell of a cervix has an average size of about 60 μm and the nucleus has a size of 5 to 7 μm. When the cell becomes cancerous, the cell division frequency increases abnormally and the nucleus grows to a size of 10 to 15 μm. As a result, an N/C ratio (nucleus size/cell size) increases to a value larger than that of a normal cell.

Thus, by detecting the sizes of a cell and the nucleus, there can be obtained an indicator that is used to determine whether the cell is cancerous or not.

Thus, in the present embodiment, the scattered light from a measurement sample flowing in the flow cell 45 is detected by the photodiode 47 and the fluorescence from the measurement sample flowing in the flow cell 45 is detected by the photomultiplier 51.

The signal processing section 7 of the measurement apparatus 2 acquires, from the scattered light signal outputted from the photodiode 47, a pulse width of the scattered light signal having a value reflecting the size of the measurement target cell and acquires, from the fluorescence signal outputted from the photomultiplier 51, a pulse width of the fluorescence signal having a value reflecting the size of the nucleus of the measurement target cell.

Then, based on the values obtained by the signal processing section 7 that reflect the size of the measurement target cell and the size of the nucleus of the measurement target cell, whether the measurement target cell is abnormal or not is determined by the CPU 34 of the data processing apparatus 4 configuring an analysis section.

Specifically, the CPU 34 of the data processing apparatus 4 determines that the measurement target cell is abnormal when a value obtained by dividing the pulse width of the fluorescence signal by the pulse width of the scattered light signal is larger than a predetermined threshold value.

[Configuration of Sub Detecting Section]

The sub detection section 14 for performing preliminary detection of the sample preparation apparatus 3 detects, in a preprocessing step for preparing a sample, the number of measurement target cells in a biological sample. In the present embodiment, the flow cytometer 10 is used that has substantially the same configuration as those of the flow cytometers illustratively shown in FIG. 5 and FIG. 6.

The sample preparation apparatus 3 of the present embodiment preliminarily measures the concentration of measurement target cells prior to the main measurement by the measurement apparatus 2. Accordingly, it is sufficient for the sub detecting section 14 to output a signal for counting the number of the cells.

Thus, in the case of the flow cytometer 10 configuring the sub detecting section 14, it is only required to acquire a forward scattered light signal (FSC). Thus, the photomultipliers 50 and 51 for acquiring a side scattered light signal (SSC) and a side fluorescence signal (SFL) are not provided and only the photodiode 47 for acquiring FSC is provided.

Then, the optical signal received by the photodiode 47 of the sub detecting section 14 as described above is converted to an electric signal and is amplified. Then, the resultant signal is sent to the signal processing section 15 of the sample preparation apparatus 3 (FIG. 3).

The signal FSC processed by the signal processing section 15 of the sample preparation apparatus 3 is sent to the preparation control section 16. The microprocessor 19 of the preparation control section 16 counts the number of the measurement target cells based on the signal FSC.

The microprocessor 19 acquires the volume of biological sample preliminarily extracted by the specimen pipette section 26 for concentration measurement from a flow rate sensor (not shown) provided in the pipette section 26. By dividing the number of the cells obtained from the signal FSC by the volume, the concentration of the biological sample is calculated.

However, it is not always required to calculate the concentration itself of the biological sample. When the extraction amount of the biological sample is retained at a fixed level, the number of cells itself functions as information reflecting the concentration thereof. In other words, the concentration information generated by the microprocessor 19 of the preparation control section 16 may be not only the concentration of the biological sample but also may be other information substantially equivalent to the concentration.

Then, the microprocessor 19 of the preparation control section 16 issues, based on the above concentration information generated by the microprocessor 19, control instructions for controlling the preparation operation performed by the preparation device section 18 to the biological sample (e.g., operation for quantifying the biological sample or reagent). It is noted that specific contents of the control will be described later.

[Fluid Circuit of Preparation Device Section]

Figure 7:
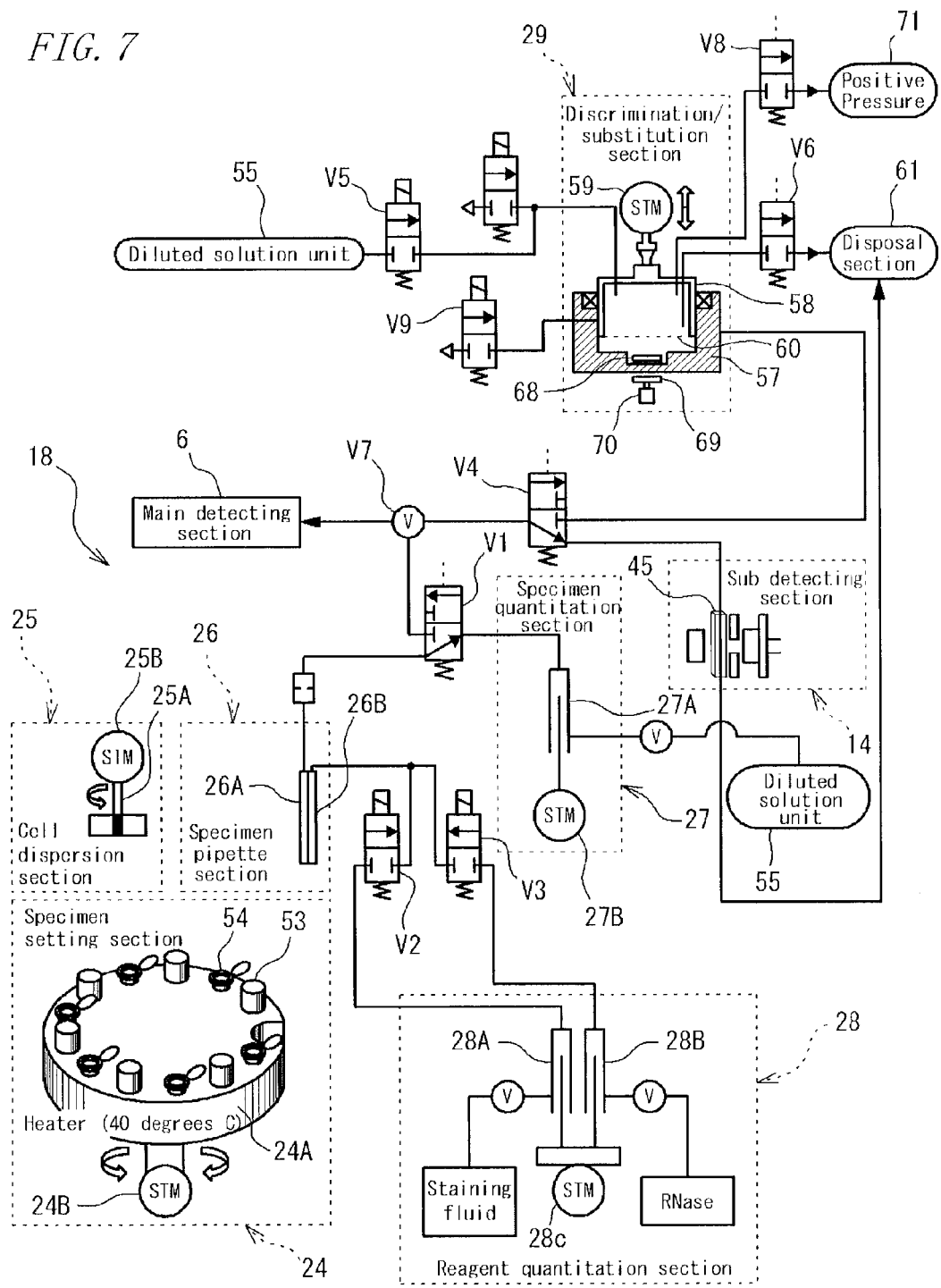
FIG. 7 is a fluid circuit diagram of a preparation device section.

FIG. 7 is a fluid circuit diagram of the preparation device section 18.

As shown in FIG. 7, the specimen setting section 24 comprises: a circular rotation table 24A; and a driving section 24B for driving the rotation of the rotation table 24A. At the outer periphery of the rotation table 24A, there is provided a retention section that can set the living body container 53 for storing mixed liquid of the biological sample and preservative solution and a product container (microtube) 54 for storing the product generated through the discrimination/substitution processing by the discrimination/substitution section 29.

The cell dispersion section 25 comprises: an agitation bar 25A for agitating the sample in the living body container 53; and a driving section 25B for driving the rotation of the agitation bar 25A. The driving section 25B inserts the agitation bar 25A into the living body container 53 to rotate the agitation bar 25A.

As a result, the biological sample in the living body container 53 is agitated and the cells included in the biological sample can be dispersed.

The specimen pipette section 26 comprises: the first pipette 26A that sucks the biological sample in the living body container 53 to supply the sample to the specimen quantitation section 27 and to return the product generated by the discrimination/substitution section 29 to the product container 54; and the second pipette 26B that supplies reagent such as staining fluid quantified by the reagent quantitation section 28 to the product container 54.

The first pipette 26A is connected via a pipe line to a storage container 57 of the discrimination/substitution section 29 which will be described later. Thus, liquid for which the measurement target cells are discriminated by the discrimination/substitution section 29 can be returned by the first pipette 26A to the product container 54.

The specimen quantitation section 27 comprises: a quantitation cylinder 27A; and a driving section 27B for moving a quantitation piston inserted in the cylinder 27A in the up-and-down direction. The quantitation cylinder 27A is connected by a pipe line to the first pipette 26A via a direction switching valve V1.

The mixed liquid of the biological sample and the preservative solution sucked from the living body container 53 via the first pipette 26A is introduced to the quantitation cylinder 27A through the direction switching valve V1. The introduced mixed liquid of the biological sample and the preservative solution is sent to the next discrimination/substitution section 29 through the direction switching valve V1 by the travel of the quantitation piston by the driving section 27B.

It is noted that, in the present embodiment, the quantitation cylinder 27A of the specimen quantitation section 27 is also connected via a pipe line to a diluted solution unit 55 for preparing diluted solution for a biological sample.

The reagent quantitation section 28 comprises: a pair of quantitation cylinders 28A and 28B; and a driving section 28C for moving quantitation pitons respectively inserted to the cylinders 28A and 28B in the up-and-down direction. The cylinders 28A and 28B are connected by a pipe line to the second pipette 26B via supply switching valves V2 and V3, respectively.

The reagent in the reagent container is supplied to the respective quantitation cylinders 28A and 28B. The supplied reagent is quantified in a predetermined amount by the travel of the quantitation piston by the driving section 28C. Then, the quantified reagent is sent to the second pipette 26B via the supply switching valves V2 and V3.

Thus, the discriminated sample returned to the product container 54 of the specimen setting section 24 can be mixed with a plurality of types of reagents in predetermined amounts quantified by the reagent quantitation section 28.

In the present embodiment, there are two types of reagents quantified by the respective quantitation cylinders 28A and 28B of the reagent quantitation section 28. Among these reagents, the reagent that is measured by one quantitation cylinder 28A and that is added to a biological sample is staining liquid for performing PI staining. The reagent that is measured by the other quantitation cylinder 28B and that is added to the biological sample is RNase for subjecting cells to an RNA processing. The PI staining is performed by propidium iodide (PI) that is fluorescence staining fluid including dye. In the PI staining, a nucleus is selectively stained. Thus, the fluorescence from the nucleus can be detected. The RNA processing is a processing for dissolving RNA in the cell. The staining liquid stains both of the RNA and DNA of an epidermal cell. Thus, RNA is dissolved by performing the above RNA processing and is not stained by the staining liquid, so that the cell nucleus DNA can be measured accurately.

The discrimination/substitution section 29 comprises: the storage container 57 having an opening shape at the upper part; a filtration cylinder 58 inserted to the storage container 57 so as to be movable in the up-and-down direction; and a driving section 59 for moving the filtration cylinder 58 in the up-and-down direction in the storage container 57.

The storage container 57 is connected by a pipe line to the quantitation cylinder 27A of the specimen quantitation section 27 via the direction switching valves V1, V7, and V4. Thus, the mixed liquid of the biological sample and the preservative solution quantified by the specimen quantitation section 27 is supplied via the direction switching valves V1, V7, and V4 to the storage container 57 and can be once retained in the interior of the container 57. The already-discriminated biological sample in the storage container 57 is sent via the same path to the first pipette 26A.

Furthermore, the storage container 57 is connected to the exterior of the storage container 57 via the switching valve V9. By opening the switching valve V9, the interior of the storage container 57 can be opened to air.

The pipe line part from the direction switching valve V4 to the disposal section 61 includes the flow cell 45 of the sub detecting section 14. Thus, the sub detecting section 14 can count the number of the cells of the already-discriminated biological sample discharged from the storage container 57.

The filtration cylinder 58 is composed of a hollow tube having a filter 60 at the lower part that does not allow a measurement target cell (epidermal cell) to pass therethrough and that allows cells having a smaller diameter than that of the measurement target cell (e.g., red blood cells, white blood cells) to pass therethrough. The filtration cylinder 58 is connected via a pipe line to the diluted solution unit 55 via the switching valve V5.

Thus, the diluted solution of the diluted solution unit 55 can be supplied to the interior of the filtration cylinder 58 by opening the switching valve V5.

The driving section 59 of the discrimination/substitution section 29 causes the filtration cylinder 58 to travel in the downward direction to the storage container 57 containing therein the mixed liquid of the biological sample, the preservative solution, and the diluted solution. Then, the filter 60 of the filtration cylinder 58 downwardly moves in the mixed liquid in the storage container 57. As a result, liquid mainly including the measurement target cell remains as residual liquid at the lower part of the filter 60. At the same time, liquid mainly including the other cells and foreign substances remains as filtrate at the upper part of the filter 60 (the interior of the filtration cylinder 58).

The filtration cylinder 58 is connected by a pipe line via the switching valve V6 to the disposal section 61 of the filtrate. Thus, the filtrate filtrated by the lowering of the filtration cylinder 58 is disposed to the outside through the switching valve V6.

On the other hand, when the residual liquid after the filtration is for measuring the concentration of the biological sample, the residual liquid in the filtration cylinder 58 is sent, after the disposal of the filtrate, via the direction switching valve V4 to the flow cell 45 of the sub detecting section 14. Thereafter, the residual liquid is disposed to the disposal section 61. When the residual liquid is for preparing a measurement sample, the residual liquid is returned from the first pipette 26A to the product container 54.

As shown in FIG. 7, the quantitation cylinder 27A of the specimen quantitation section 27 is also connected by a pipe line to the main detecting section 6 of the measurement apparatus 2 via the direction switching valves V1 and V7.

The measurement sample in the product container 54 is quantified by the specimen quantitation section 27 via the first pipette 26A. Then, the sample is supplied via the valves V1 and V7 to the main detecting section 6 of the measurement apparatus 2.

It is noted that the operations of the driving section of the respective sections and the switching valves (magnet valves) V1 to V7 shown in FIG. 7 are controlled based on a control instruction from the preparation control section 16 (the microprocessor 19). The preprocessing step performed by the preparation control section 16 will be described later.

[Specific Configuration of Discrimination/Substitution Section]

Figure 8:
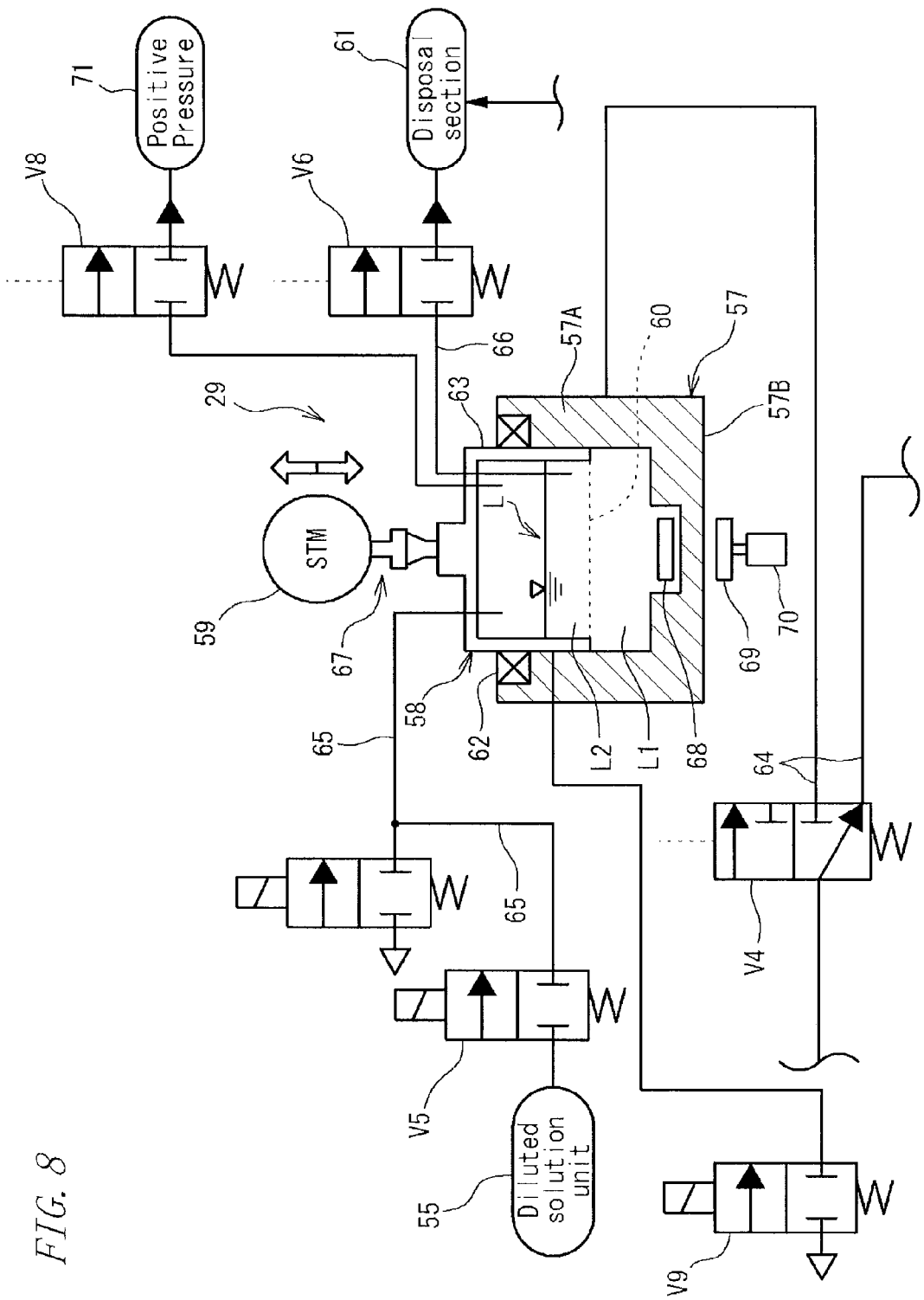
FIG. 8 is an expanded cross-sectional view illustrating a more specific configuration of a discrimination/substitution section.
Figure 9A:
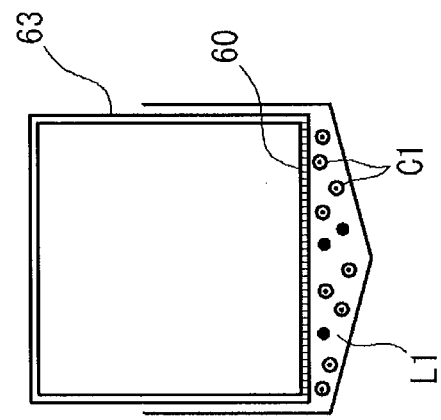
FIG. 9(a)-9(c) are explanatory diagrams showing the filtration action of the discrimination/substitution section.
Figure 9B:
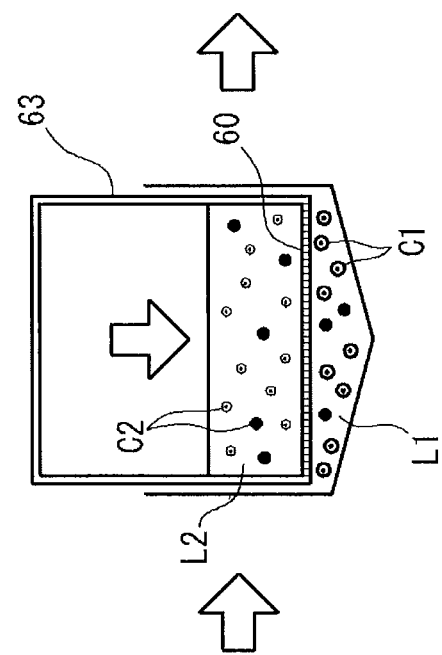

FIG. 8 is an expanded cross-sectional view illustrating a more specific configuration of the discrimination/substitution section 29. FIG. 9 is an explanatory diagram illustrating the filtration function thereof.

As shown in FIG. 8, the discrimination/substitution section 29 of the present embodiment comprises: the storage container 57 that can contain therein liquid L including a biological sample; and the filter 60 that does not allow the first cell C1 in the biological sample to pass therethrough and that allows the second cell C2 having a smaller diameter than that of the first cell C1 to pass therethrough.

Furthermore, the discrimination/substitution section 29 comprises the filtration cylinder 58 as a liquid separation section that allows the liquid L to pass the filter 60 to separate the liquid L into the first liquid L1 mainly including the first cell C1 and the second liquid L2 mainly including the second cell C2.

The storage container 57 has, in an integrated manner, a hollow body section 57A having a shaft center in the up-and-down direction and a bottom section 57B that is connected to the lower part of the body section 57A and that has a flat inner surface of which center part is concave to the lower direction.

Furthermore, the discrimination/substitution section 29 comprises, in the vicinity of the inner face of the bottom section 57B of the storage container 57, a bar-like stirrer bar (stirrer) 68 rotating by a magnetic force and, at the lower side of the bottom section 57B, a magnet 69 for giving a magnetic force to the stirrer bar 68 and a driving motor 70 for rotating the magnet 69. Thus, by rotating the magnet 69 by the driving motor 70 to thereby rotate the stirrer bar 68, the liquid in the storage container 57 can be agitated.

It is noted that the filtration cylinder 58 is connected to a positive pressure source 71 via the switching valve V8. Thus, by opening the switching valve V8, a positive pressure can be supplied to the interior of the filtration cylinder 58.

On the other hand, the filtration cylinder 58 comprises: a hollow tube-like cylinder 63 inserted into the storage container 57 via a seal member 62 so as to be movable in the up-and-down direction; and the filter 60 provided so as to seal the lower end opening of the cylinder 63.

In the present embodiment, the first cell C1 is assumed as an epidermal cell of a cervix. This epidermal cell has a size of about 20 to 80 μm (an average size is about 60 μm). A red blood cell as the second cell C2, which is smaller than the first cell C1, has a size of about 7 to 10 μm. A white blood cell as other second cell C2 has a size of about 8 to 15 μm. Foreign substance such as bacteria as other second cell C2 has a size of 1 to a few μm.

Thus, in the present embodiment, in order to prevent an epidermal cell from passing the through hole of the filter 60 even when a pressure is applied to the liquid in the storage container 57, the filter 60 is a metal CVD (Chemical Vapor Deposition) filter with a through hole having a diameter of 8 to 20 μm smaller than 20 μm. In the case of the metal CVD filter as described above, the through hole thereof is suppressed from being deformed when compared with the other resin filters or metal mesh filters and the aperture ratio can be advantageously increased.

Furthermore, the reason why the hole diameter of the filter 60 is set to 8 to 20 μm is that a diameter smaller than 8 μm frequently shows a phenomenon where the through hole is clogged with a cell or foreign substance at an early stage and a diameter exceeding 20 μm on the other hand frequently causes an epidermal cell to undesirably pass through a through hole when a pressure is applied to the liquid in the storage container 57. It is noted that the hole of the filter 60 preferably has a diameter of about 15μ.

The bottom section 57B of the storage container 57 is connected to a residual liquid pipe line 64 for introducing the already quantified biological sample and for discharging, to the outside, the residual liquid L1 for which filtration is already performed to acquire the resultant liquid. At a middle of this pipe line 64, the direction switching valve V4 is provided. Thus, the residual liquid pipe line 64 and the direction switching valve V4 configure a liquid acquisition section that is used to acquire the first liquid L1 separated by the filtration cylinder 58 functioning as a liquid separation section.

The upper wall section of the cylinder 63 is connected to the diluted solution pipe line 65 leading to the diluted solution unit 55. At a middle of this pipe line 65, the switching valve V5 is provided.

The upper wall section of the cylinder 63 is connected to the filtrate pipe line 66 that is used to dispose the filtrated filtrate L2 to the outside and that leads to the disposal section 61. At a middle of the pipe line 66, the switching valve V6 is provided. Thus, the filtrate pipe line 66 and the switching valve V6 configure a liquid discharge section for discharging, to the outside, the second liquid L2 separated by the filtration cylinder 58 functioning as a liquid separation section.

An upper end of the cylinder 63 is connected to a travel mechanism section 67 that is used to convert the rotation movement of the driving section 59 composed of a motor for example to the travel in the up-and-down direction of the cylinder 63.

The driving section 59 of the travel mechanism section 67 drives the filtration cylinder 58 in accordance with a control instruction from the preparation control section 16 (microprocessor 19).

For example, as shown in FIG. 9(*a*), the preparation control section 16 lowers the filtration cylinder 58 so that the filter 60 travels in the lower direction from the upper side of the liquid level of the liquid L in the storage container 57 (the mixed liquid of the biological sample, the preservative solution, and the diluted solution) to the interior of the liquid.

Then, as shown in FIG. 9(*b*), the liquid in which almost all cells included therein are the first cells (epidermal cell) C1 remains as the residual liquid L1 at the lower part of the filter 60 in the storage container 57. The liquid including the other second cells C2 (foreign substances such as red blood cells, white blood cells, and bacteria) remains as the filtrate L2 at the upper part of the filter 60 (the interior of the filtration cylinder 58).

Thereafter, the preparation control section 16 controls the driving section 59 of the travel mechanism section 65 so that the filter 60 already travelled into the liquid L is returned in the upper direction by a predetermined distance.

Specifically, the preparation control section 16 controls the travel mechanism section 67 so that the filtration cylinder 58 is lowered until the filter 60 reaches a lowering limit set at the bottom section 57B or in the vicinity thereof and then the filter 60 is returned in the upward direction by a predetermined distance. By returning in the upward direction, the first cell C1 attached to the lower face of the filter 60 can be separated from the filter 60.

Figure 9C:
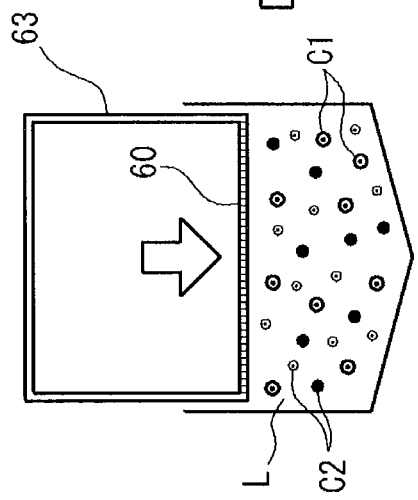

Then, the preparation control section 16 firstly releases the switching valve V6. As a result, as shown in FIG. 9(c), the filtrate L2 is discharged to the outside earlier than the residual liquid L1. Thereafter, the direction switching valve V4 is released in order to acquire the residual liquid L1.

[Contents of Analysis Processing]

Figure 10:
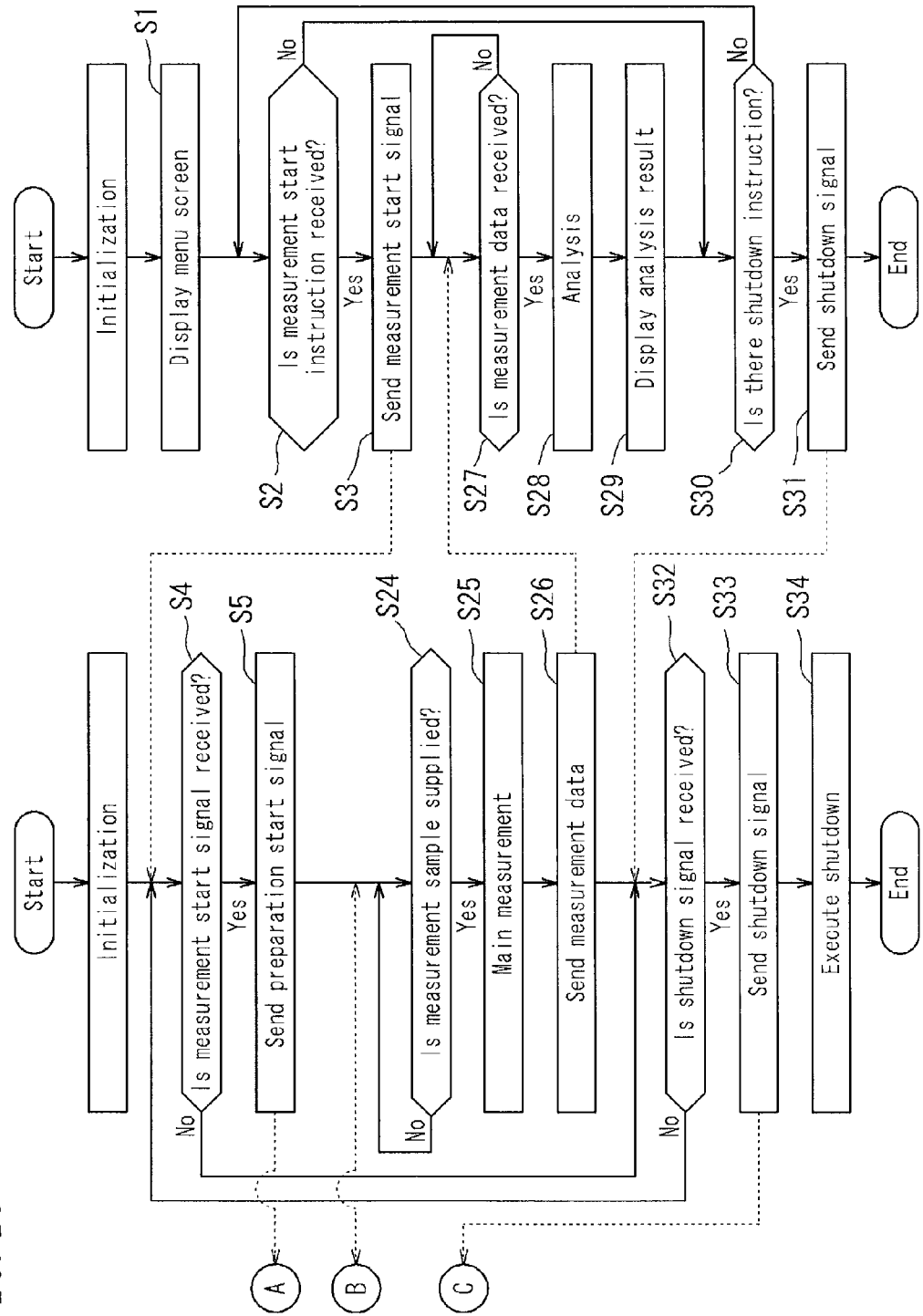
FIG. 10 is a flowchart illustrating the processings performed by the respective control sections of the cell analyzer.
Figure 11:
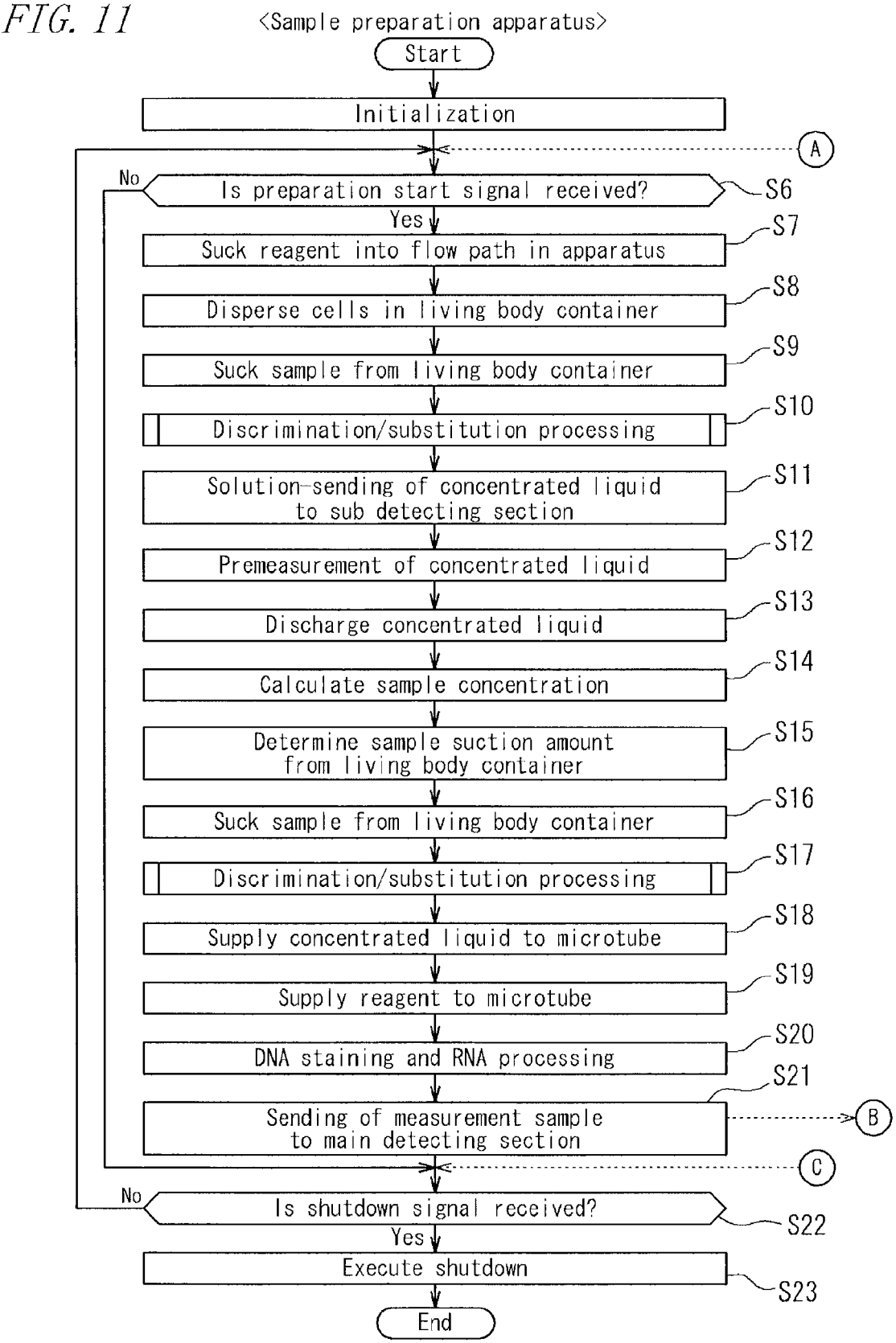
FIG. 11 is a flowchart illustrating the processings performed by the respective control sections of the cell analyzer.

FIG. 10 and FIG. 11 are a flowchart illustrating the processings performed by the respective control sections 8, 16, and 31 of the cell analyzer 1.

It is noted that FIG. 10 shows, at the right column, a processing flow performed by the control section (processing body) 31 of the data processing apparatus 4 and shows, at the left column, a processing flow performed by the control section 8 of the measurement apparatus 2. FIG. 11 shows a processing flow performed by the control section 16 of the sample preparation apparatus 3 in a single column. However, this processing flow is connected to the processing flow of FIG. 10 at the shown points A, B, and C. The following section will describe, with reference to FIG. 10 and FIG. 11, the processing contents performed by the cell analyzer 1.

First, the control section 31 of the data processing apparatus 4 causes the display section 32 to display a menu screen (Step S1). Thereafter, upon accepting a measurement starting instruction on the menu screen from the input section 33 (Step S2), the control section 31 of the data processing apparatus 4 sends a measurement starting signal to the measurement apparatus 2 (Step S3).

Upon receiving the measurement starting signal (Step S4), the control section 8 of the measurement apparatus 2 sends a preparation starting signal to the sample preparation apparatus 3 (Step S5 and point A).

Upon receiving the preparation starting signal (Step S6), the control section 16 of the sample preparation apparatus 3 sucks the reagent (staining fluid, RNase) used to prepare a measurement sample into a flow path in the apparatus and disperses, in the cell dispersion section 25, the cells in the mixed liquid of the biological sample and preservative solution including methanol as a major component contained in the living body container 53 (Steps S7 and S8).

Thereafter, the control section 16 of the sample preparation apparatus 3 causes the already-dispersed mixed liquid to be sucked by a predetermined amount from the living body container 53 into the flow path in the apparatus (Step S9) and causes the liquid to be sent to the storage container 57 of the discrimination/substitution section 29. Then, the discrimination/substitution section 29 is caused to perform a discrimination/substitution processing to the mixed liquid of the biological sample and the preservative solution (Step S10).

[Contents of Discrimination/Substitution Processing]

Figure 12:
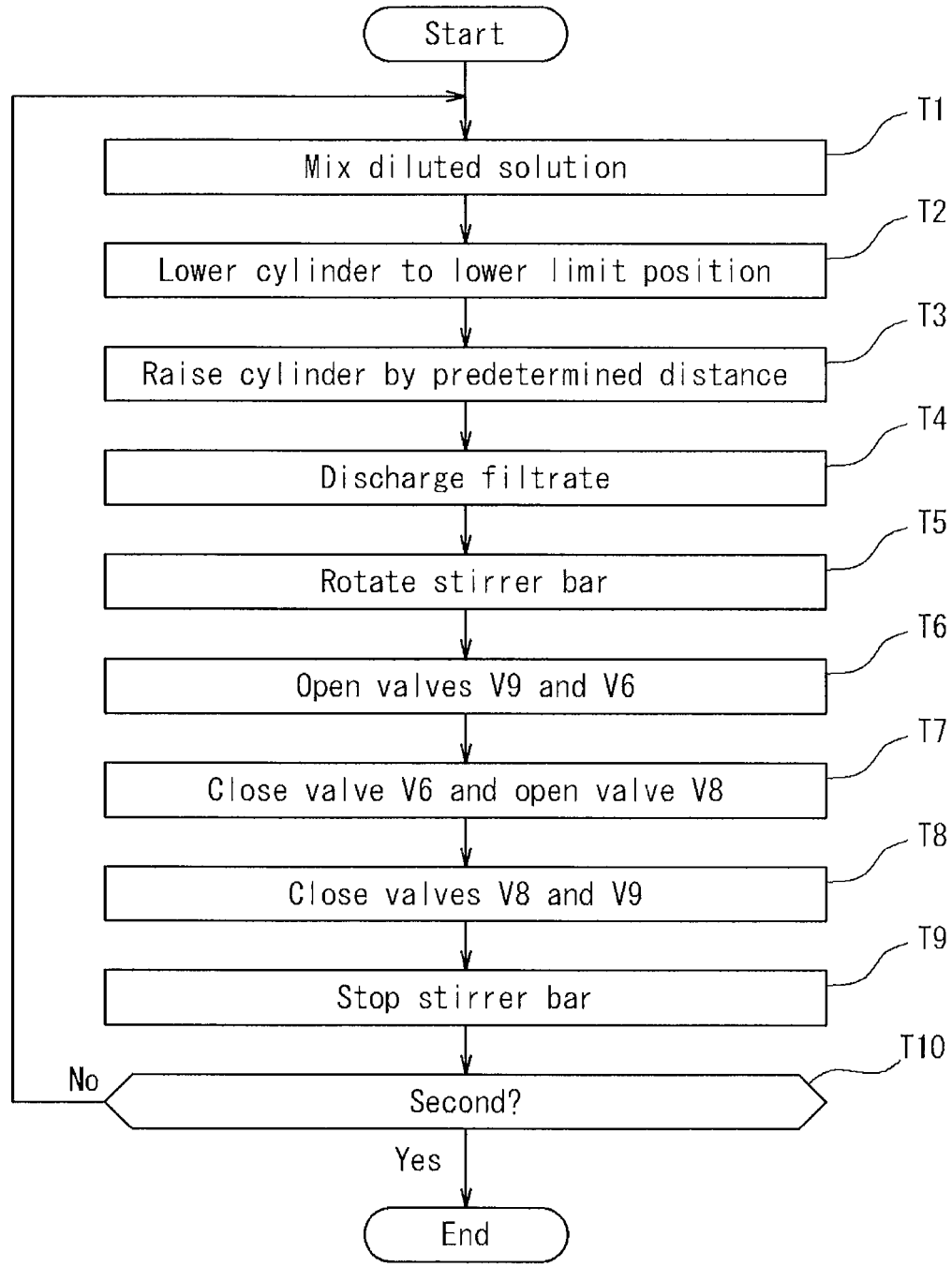
FIG. 12 is a flowchart illustrating a discrimination/substitution processing.

FIG. 12 is a flowchart illustrating the above discrimination/substitution processing.

As shown in FIG. 12, the control section 16 of the sample preparation apparatus 3 firstly causes diluted solution to be mixed with the mixed liquid of the biological sample and the preservative solution in the storage container 57 (Step T1). More specifically, the mixed liquid is supplied to the storage container 57. Then, the diluted solution is inputted to the cylinder 63 at a position slightly upper side of the lower limit. Next, the cylinder 63 is raised to the upper limit position. This consequently mixes the mixed liquid with the diluted solution.

Next, the cylinder 63 is lowered to the lower limit position (Step T2). By the lowering of the cylinder 63, the liquid L in the storage container 57 is discriminated, as described above, to a predetermined amount of the residual liquid L1 mainly including the first cell C1 as a measurement target and the filtrate L2 mainly including the cells C2 other than the first cell C1.

Thereafter, the control section 16 of the sample preparation apparatus 3 causes, at a time point at which the cylinder 63 reaches the lower limit, the cylinder 63 to be raised by a predetermined distance (Step T3). As a result, the first cell (epidermal cell) C1 attached to the lower face of the filter 60 can be floated in the concentrated liquid L1 at the lower side of the filter 60.

Thus, the travel in the processing (Step T3) for which the cylinder 63 is raised may be performed at such speed and stroke that allows the first cell C1 to be physically separated from the filter 60. The travel may be performed a plurality of times. After the above processing, the control section 16 of the sample preparation apparatus 3 discharges the filtrate L2 existing above the filter 60 to the outside (Step T4).

Next, the control section 16 of the sample preparation apparatus 3 uses the driving motor 70 to rotate the magnet 69 to thereby rotate the stirrer bar 68 in the storage container 57 (Step T5). The rotation of the stirrer bar 68 causes a circular flow in the horizontal direction in the concentrated liquid L1 in the storage container 57, thereby causing, in the lower face of the filter 60, a shearing force in the horizontal direction. Thus, the first cell (epidermal cell) C1 attached to the lower face of the filter 60 can be removed by the above shearing force and can be floated in the concentrated liquid L1 at the lower side of the filter 60. A distance between the lower face of the filter 60 (filtering area) and the filter 60-side face of the stirrer bar 68 opposed to the lower face is not particularly limited but is preferable 1 mm or less and more preferably 0.6 mm or less. The rotation number of the magnet 69 for rotating the stirrer bar 68 (i.e., the rotation number of the driving motor 70) is preferably in a range from 1000 to 2000 rpm and is more preferably about 1300 rpm.

Next, the control section 16 opens the switching valve V9 to open, to air, the space between the inner periphery face of the body section 57A of the storage container 57 and the outer periphery face of the cylinder 63 and opens the switching valve V6 to apply a negative pressure to the interior of the filtration cylinder 58 (Step T6). During this processing, the disposal section 61 is configured to function as a negative pressure source. This can consequently cause the concentrated liquid L1 existing between the inner periphery face of the body section 57A of the storage container 57 and the outer periphery face of the cylinder 63 to travel to the lower side of the filter 60. As a result, a small liquid part exists at the upper side of the filter 60.

Next, the control section 16 closes the switching valve V6 and then opens the switching valve V8 to apply positive pressure (e.g., 15 kPa) from the positive pressure source 71 into the filtration cylinder 58 for a predetermined time (e.g., 0.1 second) (Step T7). As a result, a pressure can be applied from the upper side of the filter 60 to the through hole of the filter 60. Thus, the first cell (epidermal cell) C1 clogging the through hole of the filter 60 can be removed and can be floated in the concentrated liquid L1 at the lower side of the filter 60. Furthermore, since a pressure is applied from the upper side of the filter 60 while a small liquid part being existing at the upper side of the filter 60, a pressure can be uniformly applied to a plurality of through holes of the filter 60 when compared with a case where a pressure is directly applied to the filter 60 without passing through a liquid part. Thus, the clogging of the filter 60 can be suppressed effectively.

Thereafter, the switching valves V8 and V9 are closed (Step T8). Then, the rotation of the stirrer bar 68 is stopped (Step T9).

Next, the control section 16 of the sample preparation apparatus 3 determines whether the lowering of the cylinder 63 is the second one or not (Step T10).

When the lowering of the cylinder 63 is not the second one, the control section 16 of the sample preparation apparatus 3 repeats the mixing of the diluted solution to the filtration. When the lowering of the cylinder 63 is the second one, the control section 16 of the sample preparation apparatus 3 completes the routine of the discrimination/substitution processing. It is noted that the number at which this discrimination/substitution operation is performed is not limited to two and also may be a number larger than two.

By the discrimination/substitution processing, there can be acquired such liquid that mainly includes the first cell (epidermal cell) C1 as a measurement target cell and that includes a reduced number of the second cells C2 other than the measurement target cell. Furthermore, by the above discrimination/substitution processing, the concentration of the preservative solution in the liquid (the mixed liquid of the biological sample and the preservative solution) supplied from the living body container 53 to the storage container 57 can be reduced by substituting the most part of the preservation solution with the diluted solution. Thus, in a DNA staining processing which will be described later, the influence by the preservative solution can be reduced and the DNA of the measurement target cell can be stained favorably.

Furthermore, in the discrimination/substitution processing, the substitution processing of the preservative solution and the diluted solution can be performed while the cell discrimination processing is being performed. Thus, the discrimination processing and the substitution processing can be performed with a shorter time when compared with a case where these two processings are performed separately.

Furthermore, in the discrimination/substitution processing, the stirrer bar 68 is rotated to remove the first cell (epidermal cell) C1 attached to the lower face of the filter 60 by a shearing force to float the first cell (epidermal cell) C1 in the concentrated liquid L1 at the lower side of the filter 60. A pressure is applied from the upper side of the filter 60 to the through hole of the filter 60 to thereby remove the first cell (epidermal cell) C1 clogging the through hole of the filter 60, thus allowing the first cell (epidermal cell) C1 to float in the concentrated liquid L1 at the lower side of the filter 60. Thus, the first cell (epidermal cell) C1 attached to the filter can be efficiently collected without loss.

Table 1 shows data showing to which level the epidermal cell collection rate is improved when the rotation of the stirrer bar and/or the application of a positive pressure to the through hole of the filter are/is performed.

The application of a positive pressure was performed by applying a pressure of 15 kPa for 0.1 second. Such a stirrer bar was used that is composed of a circular disk in which an upper face includes a cross-shaped convex section. This stirrer bar was rotated at 1400 rpm.

As shown in Example 6 of Table 1, the application of a positive pressure of 15 kPa provides an increase of the epidermal cell collection rate of about 35% when compared with a case where both of the positive pressure and the stirrer bar rotation are not used. Furthermore, the rotation of the stirrer bar at 1400 rpm (Examples 1, 2, 4, and 5) provides an increase of the epidermal cell collection rate of about 43 to 110% when compared with a case where both of the positive pressure and the stirrer bar rotation are not used.

Returning to FIG. 11, when the above discrimination/substitution processing (Step S10) is completed, the control section 16 of the sample preparation apparatus 3 sends to the flow cell 45 of the sub detecting section 14 the concentrated liquid (the residual liquid L1 in which most of cells included therein are epidermal cells) (Step S11). Then, the control section 16 uses the sub detecting section 14 to subject the concentrated liquid L1 to a premeasurement by a flow cytometry technique (Step S12).

This premeasurement is to obtain, prior to the main measurement performed by the measurement apparatus 2 for cancer determination, such concentration information that reflects the concentration of the measurement target cells (epidermal cells) C1 included in the biological sample. For example, this premeasurement is performed by detecting the number of the cells C1 included in the concentrated liquid L1.

[Use of Concentration Information]

Next, the control section 16 of the sample preparation apparatus 3 discharges the concentrated liquid L1 to the disposal section 61 (Step S13) and calculates the concentration of the biological sample (Step S14). Then, based on the concentration information, the control section 16 determines the suction amount of the biological sample for preparing a measurement sample for the main measurement (Step S15).

For example, when it is assumed that the suction amount of the biological sample used for the premeasurement is 200 µl and the premeasurement result shows that the number of the cells C1 is 10,000, the concentration of biological sample can be calculated as 10000/200 µl=50 (number of cells/µl)=50000 (number of cells/ml).

On the other hand, when assuming that the number of significant cells required to detect cancer cells in the main measurement is 100,000 for example, the extraction amount of the biological sample required to perform the main measurement so as to secure the number of the significant cells may be computed as 100,000÷50000 (number of cells/ml)=2 ml.

Thus, the control section 16 of the sample preparation apparatus 3 sucks the biological sample from the living body container 53 by the required amount (Step S16). Then, the control section 16 subjects the biological sample to the above-described discrimination/substitution processing again (Step S17).

TABLE 1

| | Sample type | Rotation of stirrer bar [1400 rpm] | Application of positive pressure [15 kPa] | Number of single epidermal cells | Increase rate of single epidermal cells [%] |
|---|---|---|---|---|---|
| Example 1 | A | Yes | No | 37136 | 210 |
| Example 2 | A | Yes | Yes | 40950 | 231 |
| Example 3 | A | No | Yes | 23890 | 135 |
| Example 4 | B | Yes | No | 55668 | 143 |
| Example 5 | B | Yes | Yes | 63810 | 164 |
| Example 6 | B | No | Yes | 52596 | 135 |
| Comparative Example 1 | A | No | No | 17692 | 100 |
| Comparative Example 1 | B | No | No | 38996 | 100 |

As described above, the control section 16 of the sample preparation apparatus 3 determines, based on the concentration information for the cell C1 generated by the control section 16, the amount of the biological sample for the preparation of the measurement sample used for the main measurement and controls the preparation device section 18 of the sample preparation apparatus 3 so as to acquire the determined amount of the biological sample.

In this case, the control section 16 of the sample preparation apparatus 3 determines a higher amount of the biological sample used for the preparation of the measurement sample as the cells C1 in the biological sample has a lower concentration and determines a lower amount of the biological sample used for the preparation of the measurement sample as the cells C1 in the biological sample has a higher concentration.

It is noted that, in the control section 16 of the sample preparation apparatus 3, the number of the cells C1 detected by the main detecting section 34 is not limited to the above 100,000 as the number of significant cells for cancer detection. Thus, the amount of the biological sample for the preparation of the measurement sample may be determined so as to be within a predetermined range such as 100,000 to 150,000.

Furthermore, the control section 16 of the sample preparation apparatus 3 also can determine, based on the concentration information for the cells C1 generated by the control section 16, not only the amount of the biological sample but also the amount of reagent for the preparation of the measurement sample. Then, the control section 16 can control the preparation device section 18 of the sample preparation apparatus 3 so as to acquire the determined amount of reagent.

Furthermore, the control section 16 of the sample preparation apparatus 3 also can determine, based on the concentration information for the cells C1 generated by the control section 16, the amount of at least one of the biological sample and the reagent so that the ratio between the number of the cells C1 in the biological sample and the amount of the reagent (e.g., staining fluid) is within a predetermined range. Then, the control section 16 can control the preparation device section 18 of the sample preparation apparatus 3 so as to acquire the determined amount of the biological sample or the reagent.

[Preparation of Measurement Sample]

Next, the control section 16 of the sample preparation apparatus 3 supplies, to a product container (microtube) 54, the concentrated liquid L1 obtained through the second discrimination/substitution processing (Step S18) and supplies the staining fluid and RNase stored in the apparatus from the reagent quantitation section 28 to the product container 54 (Step S19). Then, the control section 16 causes DNA staining and RNA processing to be performed in the product container 54 to thereby prepare a measurement sample (Step S20).

After the above processing, the control section 16 of the sample preparation apparatus 3 sends the resultant measurement sample to the main detecting section 6 of the measurement apparatus 2 (Step S21 and point B).

It is noted that the control section 16 of the sample preparation apparatus 3 always determines whether a shutdown signal from the measurement apparatus 2 is received or not (Step S22 and point C). When the signal is not received, the processing returns to Step S6 for determining whether the preparation starting signal is received or not. When the signal is received, the processing executes the shutdown to thereby complete the sample preparation processing (Step S23).

[Main Measurement by Measurement Apparatus and Analysis of Resultant Data]

Returning to FIG. 10, the control section 8 of the measurement apparatus 2 always determines, after sending a preparation starting signal, whether the measurement sample is supplied from the sample preparation apparatus 3 or not (Step S24).

Thus, when the measurement sample is sent from the sample preparation apparatus 3 (point B), the control section 8 of the measurement apparatus 2 sends the measurement sample to the flow cell 45 of the main measurement section 14 and subjects the cell C1 of the measurement sample to the main measurement (Step S25). Then, the control section 8 sends the measurement data to the data processing apparatus 4 (Step S26).

On the other hand, the control section 31 of the data processing apparatus 4 always determines, after sending the measurement starting signal, whether the measurement data is received from the measurement apparatus 2 or not (Step S27).

Upon receiving the above measurement data from the measurement apparatus 2, the control section 31 of the data processing apparatus 4 uses the measurement data to analyze the cell or nucleus to determine whether the cell in the measurement sample is cancerous or not for example (Step S28).

The control section 31 of the data processing apparatus 4 causes the above analysis result to be displayed on the display section 32 (Step S29) and determines whether there is a shutdown instruction by user input or not (Step S30).

When there is the above shutdown instruction, the control section 31 of the data processing apparatus 4 sends a shutdown signal to the measurement apparatus 2 (Step S31).

The control section 8 of the measurement apparatus 2 always determines whether the above shutdown signal from the data processing apparatus 4 is received or not (Step S32). When the signal is not received, the processing returns to Step S4 for determining whether a measurement starting signal is received or not. When the signal is received, the above shutdown signal is transferred to the sample preparation apparatus 3 (Step S33) and the shutdown is executed to thereby complete the measurement processing (Step S34).

As described above, according to the cell analyzer 1 of the present embodiment, liquid mainly including the first cells C1 having a larger diameter is directly acquired as liquid. This can consequently eliminate the need to separate measurement target cells captured by a filter from the filter to collect the cells, thus easily collecting the first cells C1 as measurement target cells.

Thus, measurement target cells discriminated by a filter from other cells can be easily collected. At the same time, the use of the measurement target cells thus collected can provide an easy preparation of a measurement sample suitable for the analysis of a measurement target cell by the sample preparation apparatus 3. Thus, the measurement result also can be acquired for which an influence by cells other than the measurement target cell is reduced and the measurement target cell can be analyzed accurately.

[Second Embodiment]

Figure 13:
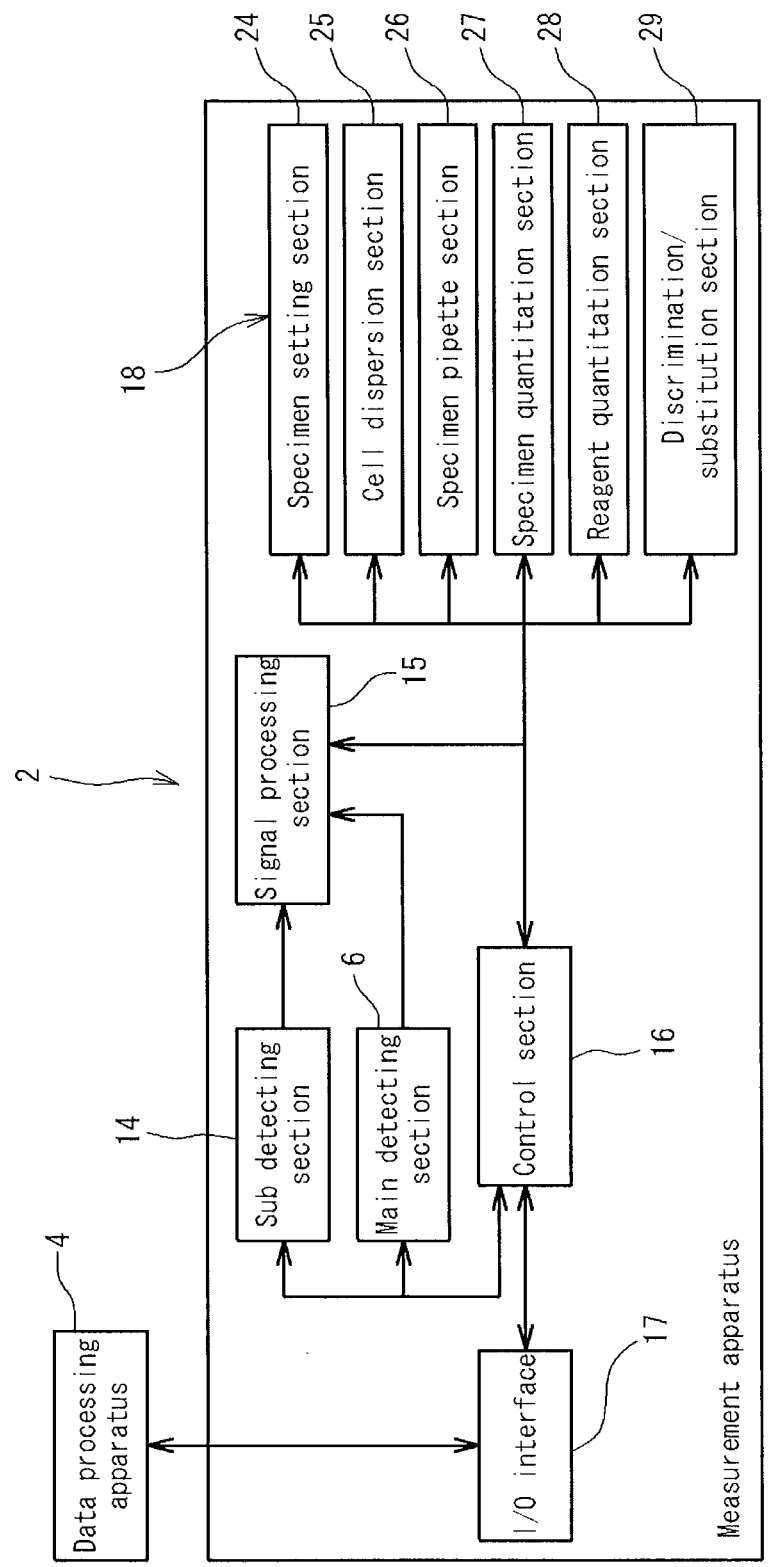
FIG. 13 is a block diagram illustrating the internal configuration of a cell analyzer according to the second embodiment.

FIG. 13 is a block diagram illustrating the internal configuration of the cell analyzer 1 according to the second embodiment of the present invention.

The cell analyzer 1 of the second embodiment is different from that of the first embodiment in that all devices required for the premeasurement performed by the sample preparation apparatus 3 are integratedly provided in the interior of the measurement apparatus 2. The respective components have the same configurations and functions as those in the first embodiment.

Thus, the configurations and functions of the respective sections of the measurement apparatus 2 will not be described further by attaching the reference numerals used in the first embodiment also to the respective sections of FIG. 13.

Figure 14:
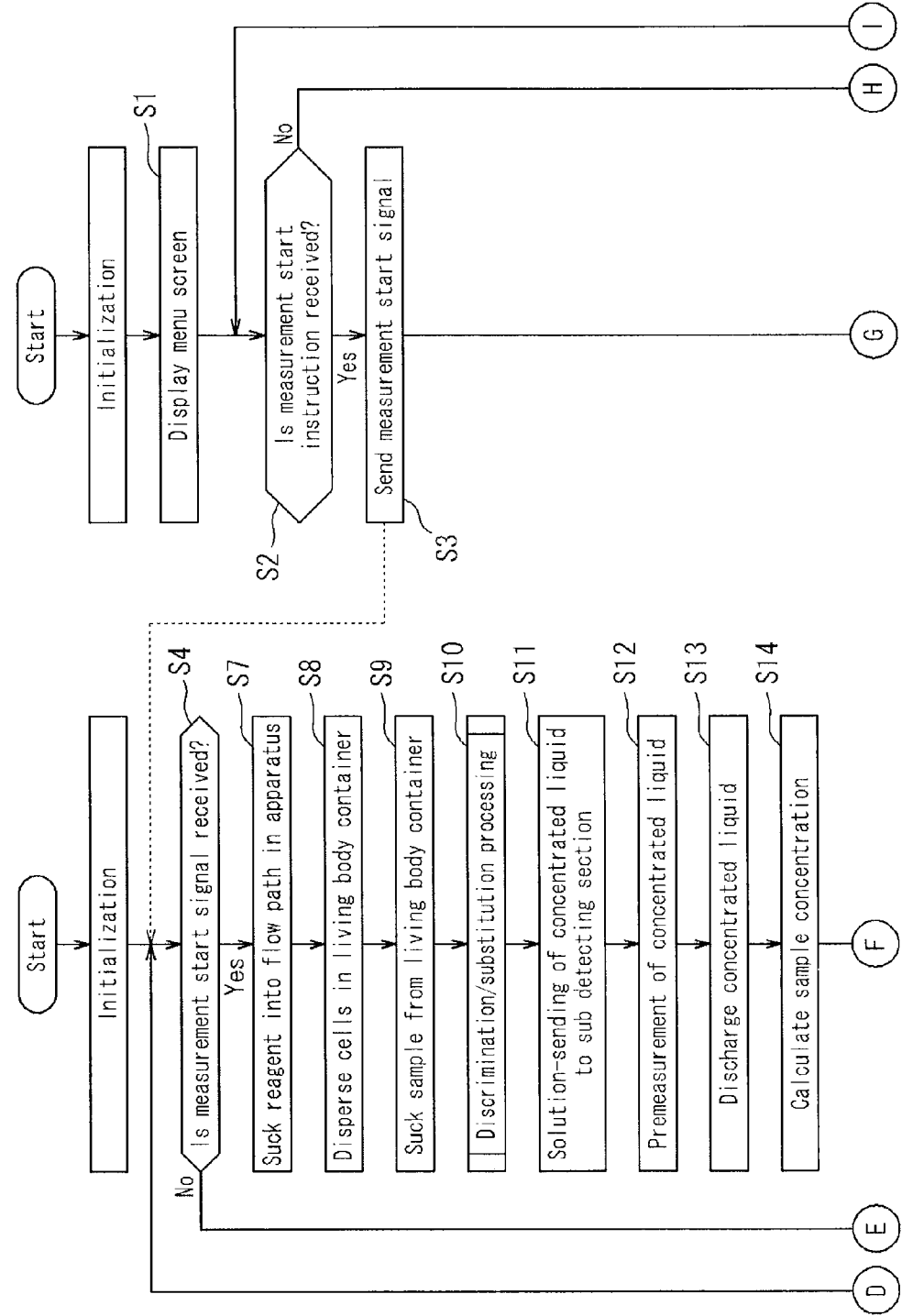
FIG. 14 shows the first half of a flowchart illustrating the processings performed by the respective control sections of the cell analyzer according to the second embodiment.
Figure 15:
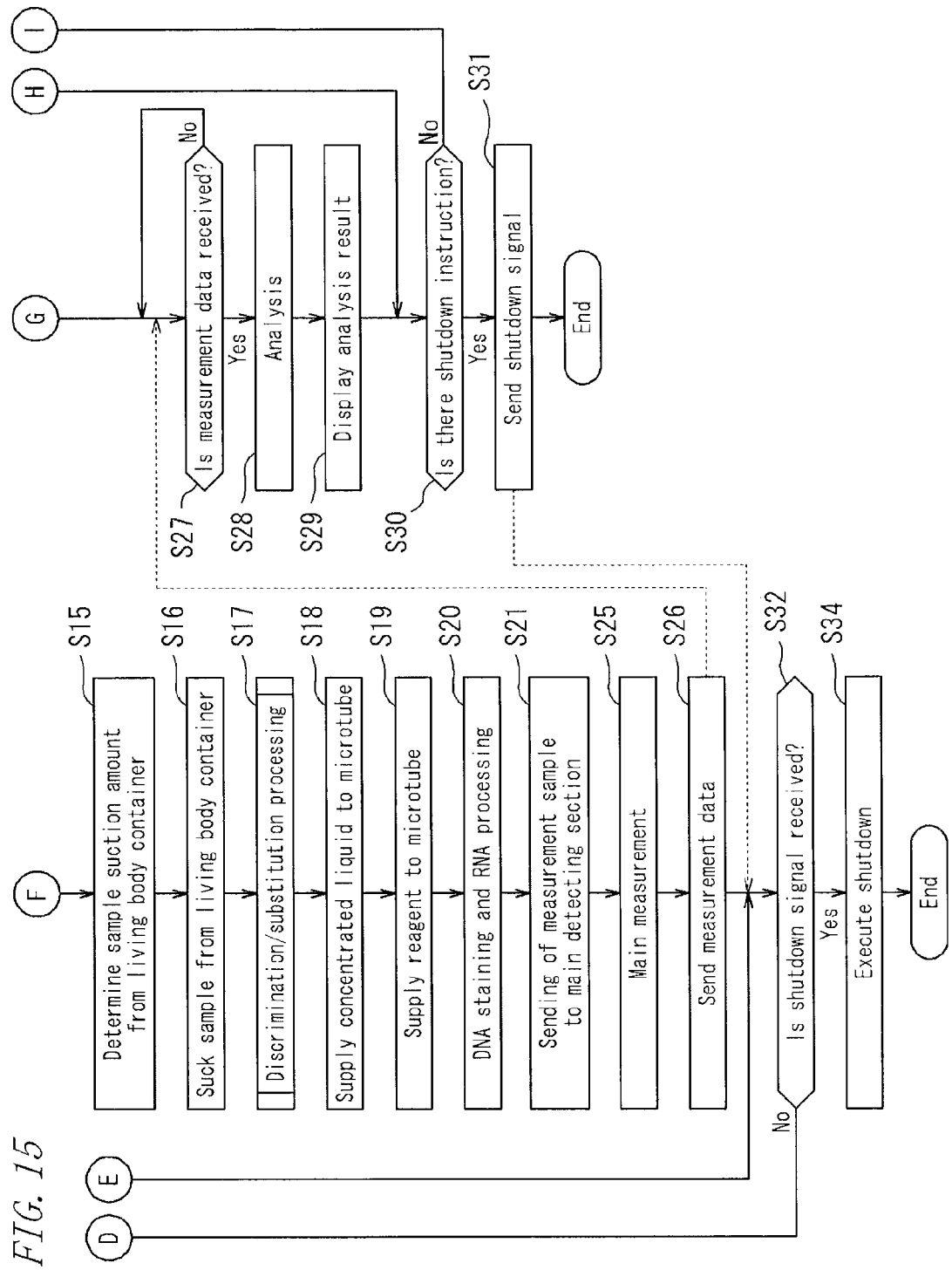
FIG. 15 shows the second half of a flowchart illustrating the processings performed by the respective control sections of the cell analyzer according to the second embodiment.

FIG. 14 and FIG. 15 are the first half and the second half of a flowchart illustrating the processings performed by the respective control sections 8 and 31 of the cell analyzer 1 according to the second embodiment, respectively. It is noted that D to I of FIG. 14 are connected to D to I of FIG. 15, respectively.

As shown in FIG. 14, the control section 31 of the data processing apparatus 4 firstly causes the display section 32 to display a menu screen (Step S1). Thereafter, when a measurement starting instruction based on the menu screen is accepted from the input section 33 (Step S2), the control section 31 of the data processing apparatus 4 sends a measurement starting signal to the measurement apparatus 2 (Step S3).

Then, in the present embodiment, the control section 8 of the measurement apparatus 2 also performs the processing performed in the first embodiment by the control section 16 of the sample preparation apparatus 3.

In other words, when the control section 8 of the measurement apparatus 2 receives a measurement starting signal (Step S4), the control section 8 sucks the reagent used for the preparation of a measurement sample (staining fluid, RNase) into the flow path in the apparatus. The control section 8 also causes, in the cell dispersion section 25, the dispersion of the cells in mixed liquid of a biological sample and preservative solution including methanol as a major component contained in the living body container 53 (Steps S7 and S8).

Thereafter, the control section 8 of the measurement apparatus 2 performs the same processing as in the control section 16 of the sample preparation apparatus 3 in the first embodiment until the measurement sample is sent to the main detecting section 6 (Steps S7 to S21).

Then, the control section 8 of the measurement apparatus 2 performs, after sending the measurement sample to the flow cell 45 of the main detecting section 6, the main measurement to the cell C1 of the measurement sample (Step S25) and sends the measurement data to the data processing apparatus 4 (Step S26).

On the other hand, the control section 31 of the data processing apparatus 4 always determines, after sending the measurement starting signal, whether the measurement data is received from the measurement apparatus 2 or not (Step S27).

Upon receiving the above measurement data from the measurement apparatus 2, the control section 31 of the data processing apparatus 4 uses the measurement data to analyze the cell or nucleus to determine whether the cell in the measurement sample is cancerous or not for example (Step S28).

Furthermore, the control section 31 of the data processing apparatus 4 causes the above analysis result to be displayed on the display section 32 (Step S29) and determines whether there is a shutdown instruction by user input or not (Step S30).

When there is the above shutdown instruction, the control section 31 of the data processing apparatus 4 sends a shutdown signal to the measurement apparatus 2 (Step S31).

The control section 8 of the measurement apparatus 2 always determines whether the above shutdown signal from the data processing apparatus 4 is received or not (Step S32). When the signal is not received, then the processing returns to Step S4 for determining whether a measurement starting signal is received or not. When the signal is received, the shutdown is executed to thereby complete the measurement processing (Step S34).

[Other Modified Examples]

It is noted that the above disclosed embodiment is an illustration of the present invention and is not the limited one. The scope of the present invention is shown not by the above embodiment but by the claims and includes all modifications equivalent to the configurations in the claims.

For example, the reagent storage section is not required to be included in the fluid circuit in the apparatus as shown in FIG. 7. Thus, another configuration also may be used where reagent in a storage section exterior to the apparatus is introduced via the reagent quantitation section 28 to the fluid circuit.

Furthermore, in the above embodiment, after the concentration of the epidermal cell C1 of a cervix is measured, a biological sample is newly sucked through the living body container 53 to supply the sample to the discrimination/substitution section 29, and the concentrated liquid C1 discriminated again is used to prepare a measurement sample. However, the concentrated liquid C1 used for the concentration measurement of the epidermal cell C1 also can be directly used as material of a measurement sample.

Furthermore, although the epidermal cell C1 of a cervix is assumed as a measurement target cell in the above embodiment, cancerous determination also can be performed on buccal cells, other epidermal cells such as bladder and pharyngeals as well as epidermal cells of organs.

Furthermore, in the above embodiment, the main detecting section 6 and the sub detecting section 14 are provided separately. However, an apparatus configuration also can be used where these detecting sections 6 and 14 are both provided by one flow cytometer 10.

Furthermore, the sub detecting section 14 for counting the number of the cell C1 in the biological sample is not limited to the optical one such as the flow cytometer 10 and also may be an electric resistance-type cell detector.

Furthermore, in the above embodiment, the liquid in the living body container 53 (the mixed liquid of the biological sample and the preservative solution) is sucked by the pipette 26A and the sucked liquid is supplied via a pipe line to the storage container 57 of the discrimination/substitution section 29. However, another configuration also may be used where the pipette 26A is configured as the mobile one, and the liquid in the living body container 53 is sucked by the pipette 26A and then the pipette 26A is caused to travel to the storage container 57 of the discrimination/substitution section 29 to subsequently discharge the liquid from the pipette 26A to the storage container 57.

Furthermore, the discrimination/substitution section 29 uses a closed system and the filtration cylinder 58 is allowed to travel in the storage container 57 in the up-and-down direction to thereby separate the liquid L in the storage container 57 into the first liquid L1 and the second liquid L2. However, another configuration also may be used where the discrimination/substitution section 29 uses an open system and a negative pressure is applied to the interior of the filtration cylinder 58 and the filtration cylinder 58 is allowed to travel in the downward direction so as to follow the rise of the liquid level of the first liquid L1, thereby separating the liquid L in the storage container 57 into the first liquid L1 and the second liquid L2.

Furthermore, in the above embodiment, the filter 60 is caused to travel downward from the upper side of the liquid level of the liquid L in the storage container 57 (the mixed liquid of the biological sample and the diluted solution) into the liquid to thereby separate the liquid L to the liquid L1 and the liquid L2. However, another configuration also may be used where the filter 60 is fixed at a predetermined position in the storage container 57 and the liquid L is allowed to pass through the filter 60 to thereby separate the liquid L into the liquid L1 and the liquid L2. For example, a configuration also may be used where the filter 60 is fixed at a predetermined position at the lower side in the storage container 57 and the liquid L in an amount for increasing the liquid level to the upper part of the filter 60 is introduced from the lower side of the filter 60 into the storage container 57 to thereby allow the liquid L to pass through the filter 60 to subsequently acquire the liquid existing at the lower side of the filter 60 in the storage container 57. In this case, the specimen quantitation section 27 as well as the valves V1, V7, and V4 configure a liquid separation section for sending the liquid L through the filter 60 to separate the liquid L into the liquid L1 and the liquid L2. This configuration also can allow only cells other than an epidermal cell as a measurement target cell (e.g., red blood cells and white blood cells) to pass through the filter 60 and the epidermal cell as a measurement target cell is not allowed to pass through the filter 60 and remains in the liquid at the lower side of the filter 60 in the storage container 57. Thus, such liquid can be acquired that has a reduced number of cells other than the measurement target cell.

Furthermore, in the above embodiment, a measurement sample prepared by the sample preparation apparatus 3 is measured by a flow cytometer. However, another configuration also may be used that includes: a smear preparation apparatus for smearing a measurement sample prepared by the sample preparation apparatus 3 to a glass slide to prepare a smear; and a cell image processing apparatus for imaging the prepared smear to analyze an epidermal cell in the imaged image. Since a measurement sample for which the number of cells such as red blood cells or white blood cells is reduced is smeared to the glass slide, an epidermal cell as a measurement target cell can be analyzed accurately.

Furthermore, in the above embodiment, the liquid in the living body container 53 (mixed liquid of a biological sample and preservative solution including methanol as a major component) is introduced to the storage container 57 of the discrimination/substitution section 29 and the diluted solution is subsequently supplied into the storage container 57 and is subjected to a discrimination/substitution processing, thereby substituting the preservative solution including methanol as a major component with the diluted solution. However, another configuration also may be used where solvent suitable for the PI staining for preparing a measurement sample is substituted with preservative solution including methanol as a major component. As a result, a measurement sample can be prepared more favorably.

Furthermore, in the above embodiment, the storage container 57 is caused to be stationary and the filtration cylinder 58 is allowed to travel in the up-and-down direction to thereby separate the liquid L in the storage container 57 into the first liquid L1 and the second liquid L2. However, the present invention is not limited to this. Another configuration also may be used where the filtration cylinder 58 is caused to be stationary and the storage container 57 is allowed to travel in the up-and-down direction to thereby separate the liquid L in the storage container 57 into the first liquid L1 and the second liquid L2. Another configuration also may be used where, in synchronization with the travel of the filtration cylinder 58 in the up-and-down direction, the storage container 57 is allowed to travel in the opposite direction to thereby separate the liquid L in the storage container 57 into the first liquid L1 and the second liquid L2.

Furthermore, in the above embodiment, the stirrer bar 68 provided in the storage container 57 is rotated to thereby remove the first cell (epidermal cell) C1 attached to the lower face of the filter 60 by a shearing force. However, another configuration also may be used where the filtration cylinder 58 including the filter 60 is oscillated in the horizontal direction or the filtration cylinder 58 is rotated in the horizontal direction to thereby remove the first cell C1 attached to the lower face of the filter 60.

Furthermore, in the above embodiment, the rotation of the stirrer bar 68 is followed by the application of a pressure from the upper side of the filter 60 to the through hole of the filter 60. However, another configuration also may be used where the application of a pressure from the upper side of the filter 60 to the through hole of the filter 60 is followed by the rotation of the stirrer bar 68. Furthermore, in the above embodiment, a pressure is applied from the upper side of the filter 60 to the through hole of the filter 60 while the stirrer bar 68 is being rotated. However, another configuration also may be used where a pressure is applied to the through hole of the filter 60 while the rotation of the stirrer bar 68 is being stopped.

Furthermore, in the above embodiment, the stoppage of the rotation of the stirrer bar 68 is followed by the sending of the concentrated liquid L1 in the storage container 57 to the outside of the storage container 57. However, another configuration also may be used where the concentrated liquid L1 is sent to the outside of the storage container 57 while the stirrer bar 68 is being rotated.

We claim:

1. A sample processing apparatus comprising:
   a sample container configured to contain a sample solution including a biological sample collected from a cervix and a preservation solution, the biological sample including epidermal cells of the cervix, red blood cells, white blood cells and bacteria;
   a cell disperser configured to disperse the epidermal cells included in the sample solution contained in the sample container;
   a filtering unit which includes a first room, a second room and a filter provided between the first room and the second room, wherein the filter is configured to prevent the epidermal cells from passing therethrough and allow the red blood cells, the white blood cells and the bacteria to pass therethrough;
   a sample supplier configured to supply, into the first room, the sample solution contained in the sample container;
   a pressure generator configured to generate a pressure differential between the first room and the second room such that at least the preservation solution, the red blood cells, the white blood cells and the bacteria are moved from the first room to the second room via the filter;
   a substitution liquid supplier configured to supply, into the first room, a substitution liquid which substitutes for the preservation solution in the first room; and
   a stirrer that is arranged within the first room and is configured to rotate so as to move the epidermal cells attached to the filter into the substitution liquid in the first room.

2. The sample processing apparatus according to claim 1, wherein
   the pressure generator comprises a negative pressure source configured to apply a negative pressure into the second room.

3. The sample processing apparatus according to claim 2, wherein
the negative pressure source discharges at least the preservation solution, the red blood cells, the white blood cells and the bacteria which have been moved into the second room via the filter.

4. The sample processing apparatus according to claim 3, further comprising
a controller configured to control the substitution liquid supplier and the negative pressure source so as to repeat the supply of the substitution liquid and the discharge of at least the preservation solution, the red blood cells, the white blood cells and the bacteria.

5. The sample processing apparatus according to claim 4, wherein
the controller is configured to control the substitution liquid supplier and the negative pressure source so as to repeat the supply of the substitution liquid and the discharge of at least the preservation solution, the red blood cells, the white blood cells and the bacteria until the preservation solution within the first room is replaced with the substitution liquid.

6. The sample processing apparatus according to claim 1, wherein
the sample supplier comprises a sample flow path for supplying the sample solution into the first room.

7. The sample processing apparatus according to claim 1, wherein
the substitution liquid supplier comprises a substitution liquid flow path for supplying the substitution liquid into the first room.

8. The sample processing apparatus according to claim 1, further comprising
a positive pressure source configured to apply a positive pressure into the second room so as to move the epidermal cells attached to the filter into the substitution liquid in the first room.

9. The sample processing apparatus according to claim 1, wherein
the stirrer is configured to rotate in a direction along a filtering area of the filter.

10. The sample processing apparatus according to claim 1, wherein
a distance between the filtering area of the filter and the stirrer opposed to the filtering area is 1mm or less.

11. The sample processing apparatus according to claim 1, wherein
the filter has a through hole having a diameter of 8 to 20 µm.

12. The sample processing apparatus according to claim 1, wherein
the filtering unit has a concave on a surface which forms the first room and faces the filter, and the stirrer is arranged within the concave.

13. A sample preparing apparatus comprising:
a sample container configured to contain a sample solution including a biological sample collected from a cervix and a preservation solution, the biological sample including epidermal cells of the cervix, red blood cells, white blood cells and bacteria;
a cell disperser configured to disperse the epidermal cells included in the sample solution contained in the sample container;
a filtering unit which includes a first room, a second room and a filter provided between the first room and the second room, wherein the filter is configured to prevent the epidermal cell from passing therethrough and allow the red blood cells, the white blood cells and the bacteria to pass therethrough;
a sample supplier configured to supply, into the first room, the sample solution contained in the sample storage container;
a pressure generator configured to generate a pressure differential between the first room and the second room such that at least the preservation solution, the red blood cells, the white blood cells and the bacteria are moved from the first room to the second room via the filter;
a substitution liquid supplier configured to supply, into the first room, a substitution liquid which substitutes for the preservation solution in the first room;
a stirrer that is arranged within the first room and is configured to rotate so as to move the epidermal cells attached to the filter into the substitution liquid in the first room; and
a reagent supplier configured to supply a reagent to a liquid taken out from the first room so as to prepare a measurement sample, wherein the liquid taken out from the first room includes the substitution liquid and the epidermal cells.

14. The sample preparing apparatus according to claim 13, wherein
the reagent is a staining solution for staining the epidermal cells.

15. The sample preparing apparatus according to claim 14, wherein
the preservation solution contains alcohol.

16. The sample preparing apparatus according to claim 13, wherein
the pressure generator comprises a negative pressure source configured to apply a negative pressure into the second room.

17. The sample preparing apparatus according to claim 16, wherein
the negative pressure source discharges at least the preservation solution, the red blood cells, the white blood cells and the bacteria which have been moved into the second room via the filter.

18. The sample preparing apparatus according to claim 17, further comprising
a controller configured to control the substitution liquid supplier and the negative pressure source so as to repeat the supply of the substitution liquid and the discharge of at least the preservation solution, the red blood cells, the white blood cells and the bacteria.

19. The sample preparing apparatus according to claim 18, wherein
the controller is configured to control the substitution liquid supplier and the negative pressure source so as to repeat the supply of the substitution liquid and the discharge of the at least the preservation solution, the red blood cells, the white blood cells and the bacteria until the preservation solution within the first room is replaced with the substitution liquid.

* * * * *